US009129046B2

(12) United States Patent
Bess et al.

(10) Patent No.: US 9,129,046 B2
(45) Date of Patent: Sep. 8, 2015

(54) SYSTEMS AND METHODS FOR MANAGING A MASTER PATIENT INDEX INCLUDING DUPLICATE RECORD DETECTION

(71) Applicant: 4medica, Inc., Culver City, CA (US)

(72) Inventors: Oleg Bess, Beverly Hills, CA (US); Vannamuthu Kuttalingam, Scottsdale, AZ (US)

(73) Assignee: 4medica, Inc., Culver City, CA (US)

( * ) Notice: Subject to any disclaimer, the term of this patent is extended or adjusted under 35 U.S.C. 154(b) by 0 days.

(21) Appl. No.: 14/187,192

(22) Filed: Feb. 21, 2014

(65) Prior Publication Data

US 2014/0244300 A1    Aug. 28, 2014

Related U.S. Application Data

(60) Provisional application No. 61/768,643, filed on Feb. 25, 2013, provisional application No. 61/768,655, filed on Feb. 25, 2013, provisional application No. 61/768,666, filed on Feb. 25, 2013, provisional application No. 61/768,681, filed on Feb. 25, 2013.

(51) Int. Cl.
*G06Q 50/00* (2012.01)
*G06F 19/00* (2011.01)
*G06F 17/30* (2006.01)

(52) U.S. Cl.
CPC ........ *G06F 19/322* (2013.01); *G06F 17/30424* (2013.01)

(58) Field of Classification Search
CPC . G06F 21/10; G06F 19/322; G06F 17/30424; G06Q 50/22; G06Q 50/24

USPC .......................................... 705/2–3
See application file for complete search history.

(56) References Cited

U.S. PATENT DOCUMENTS

| | | |
|---|---|---|
| 5,664,109 A | 9/1997 | Johnson et al. |
| 6,397,224 B1 | 5/2002 | Zubeldia et al. |
| 6,760,720 B1 | 7/2004 | De Bellis |
| 7,167,858 B2 | 1/2007 | Naeymi-Rad et al. |
| 7,346,648 B1 | 3/2008 | Seliger |
| 7,409,401 B2 | 8/2008 | Hansen et al. |
| 7,428,494 B2 | 9/2008 | Hasan et al. |
| 7,440,904 B2 | 10/2008 | Hasan et al. |
| 7,475,020 B2 | 1/2009 | Hasan et al. |

(Continued)

OTHER PUBLICATIONS

"4medica Introduces the Industry's First MPI Engine based on Big Data Technologies; First-of-its kind solution for the patient identification challenge", Delivering True Clinical Integration; Los Angeles, CA <www.4medica.com>, Mar. 11, 2013.

(Continued)

*Primary Examiner* — Luke Gilligan
(74) *Attorney, Agent, or Firm* — Kwan & Olynick LLP

(57) ABSTRACT

A system for managing a master patient index is described. The master patient index database is constructed using inverted indices. The inverted index formulation enables faster, more complete and more flexible duplicate detection as compared to traditional master patient database management techniques. A master patient index management system including a remote user interface configured to leverage the inverted index formulation is described. The user interface includes features for managing records in an MPI database including identifying, efficiently comparing, updating and merging duplicate records across a heterogeneous healthcare organization.

24 Claims, 11 Drawing Sheets

(56) References Cited

U.S. PATENT DOCUMENTS

| | | |
|---|---|---|
| 7,509,264 B2 | 3/2009 | Hasan et al. |
| 7,533,030 B2 | 5/2009 | Hasan et al. |
| 7,574,432 B1 | 8/2009 | De Bellis |
| 7,707,047 B2 | 4/2010 | Hasan et al. |
| 7,725,331 B2 | 5/2010 | Schurenberg et al. |
| 7,756,728 B2 | 7/2010 | Maughan et al. |
| 8,095,386 B2 | 1/2012 | Lassetter et al. |
| 8,131,563 B2 | 3/2012 | Hasan et al. |
| 8,140,370 B2 | 3/2012 | Larsen et al. |
| 8,214,234 B2 | 7/2012 | Hasan et al. |
| 2002/0007284 A1 | 1/2002 | Schurenberg et al. |
| 2002/0138353 A1 | 9/2002 | Schreiber |
| 2003/0036927 A1 | 2/2003 | Bowen |
| 2003/0126156 A1 | 7/2003 | Stoltenberg et al. |
| 2003/0139943 A1 | 7/2003 | Dvorak et al. |
| 2006/0080312 A1 | 4/2006 | Friedlander et al. |
| 2006/0229911 A1 | 10/2006 | Gropper et al. |
| 2007/0055552 A1 | 3/2007 | St. Clair et al. |
| 2007/0192140 A1 | 8/2007 | Gropper |
| 2007/0299697 A1 | 12/2007 | Friedlander et al. |
| 2008/0046292 A1 | 2/2008 | Myers et al. |
| 2009/0080408 A1 | 3/2009 | Natoli et al. |
| 2010/0131299 A1 | 5/2010 | Hasan et al. |
| 2010/0169296 A1 | 7/2010 | King et al. |
| 2011/0004626 A1 | 1/2011 | Naeymi-Rad et al. |
| 2011/0125527 A1 | 5/2011 | Nair |
| 2011/0246237 A1 | 10/2011 | Vdovjak |
| 2011/0246238 A1 | 10/2011 | Vdovjak et al. |
| 2011/0246241 A1 | 10/2011 | Hasan et al. |
| 2012/0029932 A1 | 2/2012 | Stein et al. |
| 2012/0035961 A1 | 2/2012 | Dvorak et al. |
| 2012/0066197 A1* | 3/2012 | Rana et al. .................... 707/706 |
| 2012/0078664 A1 | 3/2012 | Hasan et al. |
| 2012/0150566 A1 | 6/2012 | Hasan et al. |
| 2012/0191475 A1 | 7/2012 | Pandey |
| 2012/0203571 A1 | 8/2012 | Crapo et al. |
| 2012/0203576 A1 | 8/2012 | Bucur et al. |
| 2013/0238621 A1* | 9/2013 | Ganjam et al. ................ 707/737 |

OTHER PUBLICATIONS

"eINDEX Single Patient View User's Guide", Sun Seebeyond, Sun Microsystems, Inc., Release 5.1.3, Retrieved from Internet <http://www.oracle.com/us/industries/healthcare/058487.pdf>, 243.

"Oracle Healthcare Master Person Index", Oracle Data Sheet, Oracle Health Sciences, Retrieved from Internet <http://www.oracle.com/us/industries/healthcare/058487.pdf>, 2012, 4 pgs.

"Powering Healthcar Transformation", MirthMatch; Retrieved from the internet <http://www.mirthcorp.com/products/mirth-match>, Feb. 21, 2014.

McCoy, Allison B. et al., "Matching identifiers in electronic health records: implications for duplicate records and patient safety", BMJ Qual Saf 2013; 22;219-224, 2013.

"4medica's Big Data MPI Executive Overview", 4medica <www.4medic.com>, 1 pgs.

* cited by examiner

Figure 10

SYSTEMS AND METHODS FOR MANAGING A MASTER PATIENT INDEX INCLUDING DUPLICATE RECORD DETECTION

CROSS-REFERENCE TO RELATED APPLICATIONS

This patent application claims priority under 35 U.S.C. §119(e) to:

a) U.S. Provisional Patent Application Ser. No. 61/768,643, filed Feb. 25, 2013, titled, "System and Method for Utilizing an Inverted Index to Perform Probabilistic Scoring for Identification of Duplicate Patient Records,"

b) U.S. Provisional Patent Application Ser. No. 61/768,655, filed Feb. 25, 2013, titled, "System and Method for Reducing Computational Requirements to Identify and Maintain Duplicate patient records in a Single or Multiple organizations,"

c) U.S. Provisional Patent Application Ser. No. 61/768,666, filed Feb. 25, 2013, titled, "System and Method for Improving the Detection Rate of Duplicate Patients in an Organization,"

d) U.S. Provisional Patent Application Ser. No. 61/768,681, filed Feb. 25, 2013, titled, "System and Method to Improve Detection Rates of Duplicate Patients by Analyzing Historical or Synonym Values," each of which is incorporated by reference in its entirety and for all purposes.

FIELD OF THE INVENTION

This invention generally relates to managing a master patient index for a healthcare organization, and more particularly to identifying and merging duplicate healthcare records in a master patient index.

BACKGROUND

A typical healthcare organization has many legacy patient records in different formats. Across the different formats, patient information is often partially duplicated where each record format varies in its level of completeness from patient to patient. To obtain a complete and single view of a patient, healthcare organizations have attempted to consolidate their legacy healthcare records.

One approach used to consolidate legacy healthcare records involves a creation of a master patient index (MPI). A master patient index (MPI) is a database that is used across a healthcare organization to maintain consistent, accurate and current demographic and essential medical data on the patients seen and managed within its various departments. An objective of an MPI is to ensure that each patient is represented only once across all the software systems used within the organization.

To generate an MPI each patient is assigned a unique identifier that is used to refer to this patient across the enterprise. Then, for each patient, the individual's legacy healthcare records are identified, matched, merged, de-duplicated, and cleansed to create a master index that may be used. The essential patient data can include name, gender, date of birth, race and ethnicity, social security number, current address and contact information, insurance information, etc.

Many hospitals and other healthcare organizations have struggled to achieve the necessary level of efficiency in the MPI management process to eliminate existing record keeping issues and reduce the likelihood that future ones will develop. Part of the problem is limited resources. The MPI management process can be time-consuming and labor-intensive, requiring dedicated human resources and special expertise which hospitals have difficulty retaining. Further, the typical MPI management process is primarily manual and therefore inefficient and prone to human error. In view of the above, new methods are needed for creating and managing MPIs.

SUMMARY

A system for managing a master patient index is described. The master patient index database is constructed using inverted indices. The inverted index formulation enables faster, more complete and more flexible duplicate detection as compared to traditional master patient database management techniques. In particular, the entire master patient index can be searched each time a query involving duplicate record detection is implemented.

A table of links based upon particular duplicate record probability scoring formulation is not utilized. Thus, the duplicate record probability scoring formulation can be easily changed and updated as new healthcare records with different levels of data reliability are added to the master patient index. In one embodiment, different duplicate probability scoring formulations can be applied to different subsets of the healthcare records within the master patient index.

One aspect of the embodiments described herein is related to a method of managing electronic protected healthcare information. The method can be generally characterized as including 1) receiving, by a processor, a plurality of healthcare records having electronic protected healthcare information wherein each healthcare record is configured with a plurality of different fields each field configured to receive at least one value; 2) storing, to a memory, a master patient index database in an inverted index format, wherein, in the inverted index format, a set of values is determined which is inclusive of all values appearing in at least one field of the healthcare records such that each value in the set of values is mapped to one or more of the plurality of healthcare records; 3) receiving, by the processor, one or more search input terms; 4) based upon the one or more search inputs terms, generating, in the processor, a search query configured to search the set of values to identify a subset of values in the set of values which match the search query; 5) determining, by the processor, using the inverted index format of the master patient index database, a set of healthcare records associated with each of the subset of values; 6) determining, by the processor, for each of the subset of the values, a contribution to a duplicate probability score; 7) based upon the determined contributions to the duplicate probability score and the set of the healthcare records determined to be associated with each of the subset of the values, determining, by the processor, for two or more healthcare records in the set of healthcare records identified via the search query a total duplicate probability score; and 8) outputting, by the processor, the total duplicate probability score and electronic protected healthcare information for each of the two or more healthcare records.

BRIEF DESCRIPTION OF THE DRAWINGS

The included drawings are for illustrative purposes and serve only to provide examples of possible structures and process steps for the disclosed inventive systems and methods for healthcare services. These drawings in no way limit any changes in form and detail that may be made to the invention by one skilled in the art without departing from the spirit and scope of the invention.

FIG. 10 is an illustration of a state of a MPI system interface showing merge history information in accordance with the described embodiments.

DESCRIPTION OF THE PREFERRED EMBODIMENTS

Figure 1:
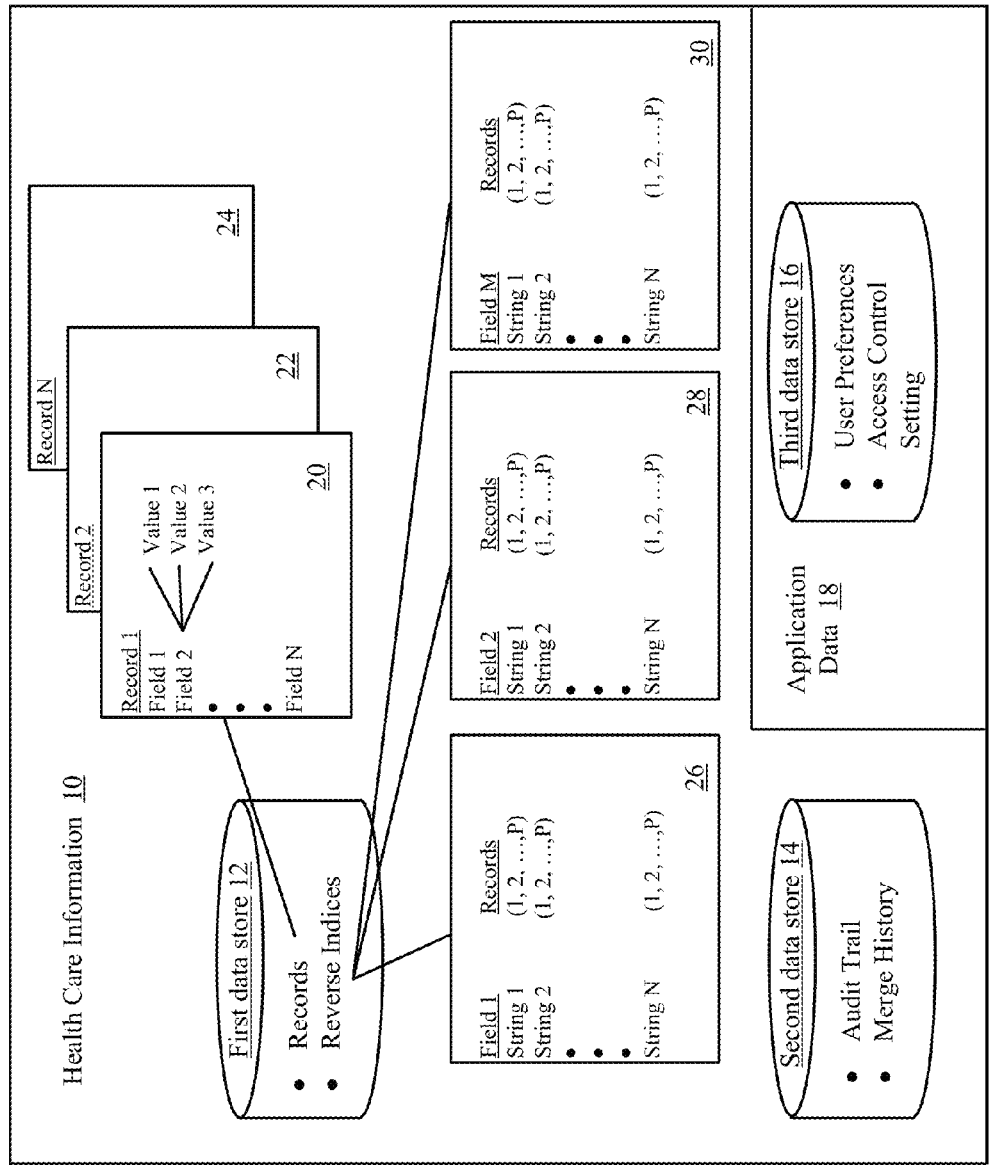
FIG. 1 is a block diagram of a system for managing healthcare information associated with a master patient index database using inverted indices in accordance with the described embodiments.

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

An accurate Master Patient Index (MPI), whether in paper, electronic or somewhere in between, can be considered one of the most important resources in a healthcare organization. However, an MPI is only a beneficial resource if it remains clean and free from duplicate medical records. Thus, an important aspect of MPI management is associated with duplicate records.

Generally, the duplicate record issue can be addressed in three ways. First, a cleaning process can be implemented where duplicate records are identified and removed from an MPI database. This type of cleaning process is usually a one-time effort that involves focusing a significant amount of resources over a limited period of time. Second, once a MPI database is cleaned, procedures can be formulated which prevent new duplicates from being introduced into the MPI database. Third, methods can be implemented which help identify duplicate records, which in spite of the procedures introduced for preventing duplicates, may have been inadvertently added to an MPI. After the duplicates are identified, tools can be provided for removing duplicates, such as tools for updating and merging records and keeping track of the changes.

Currently, automatic systems for duplicate tracking are not exact, requiring manual intervention. Further, in current systems, hardware systems are heavy CPU utilizers and do not allow for growth of the patient database. In particular, adding more patients to database logarithmically increases the hardware requirements. Further, current systems do not allow continuous tuning of the duplicate detection processes even if significant changes occur in the patient database, such adding or removing of different field types, etc. In view of the above, better apparatus and methods are needed for duplicate record detection.

As follows, methods and apparatus useful for addressing duplicate records in an MPI management system are described. In particular, a method of structuring a MPI database which enables faster and more dynamic probabilistic scoring used to identify duplicate healthcare records is described. In one embodiment, to accomplish this objective, inverted indices are constructed for the data in the MPI database. The implementation of inverted indices allows probabilistic scoring to be performed over the entire MPI database each time a record query is performed.

Once duplicate records are identified, a record management interface is provided which allows information associated with records identified as being duplicates to be displayed and to be modified. Duplicate record modification can involve updating information in one record with information from another record or merging two or more different records. The record management interface is configured to allow a user to perform these tasks in an efficient, secure, reversible and auditable manner.

In more detail, with respect to FIG. 1, a system for managing healthcare information associated with a master patient index database using inverted indices is described. With respect to FIG. 2, an MPI management system which leverages the healthcare information in the MPI database is described. For example, an application layer coupled to the MPI database, which can be accessed via a remote user interface, is discussed. With respect to FIG. 3, organization specific duplicate scoring within the MPI management system and other examples of duplicate scoring enabled using an MPI database formatted using inverted indices are discussed.

Figure 4:
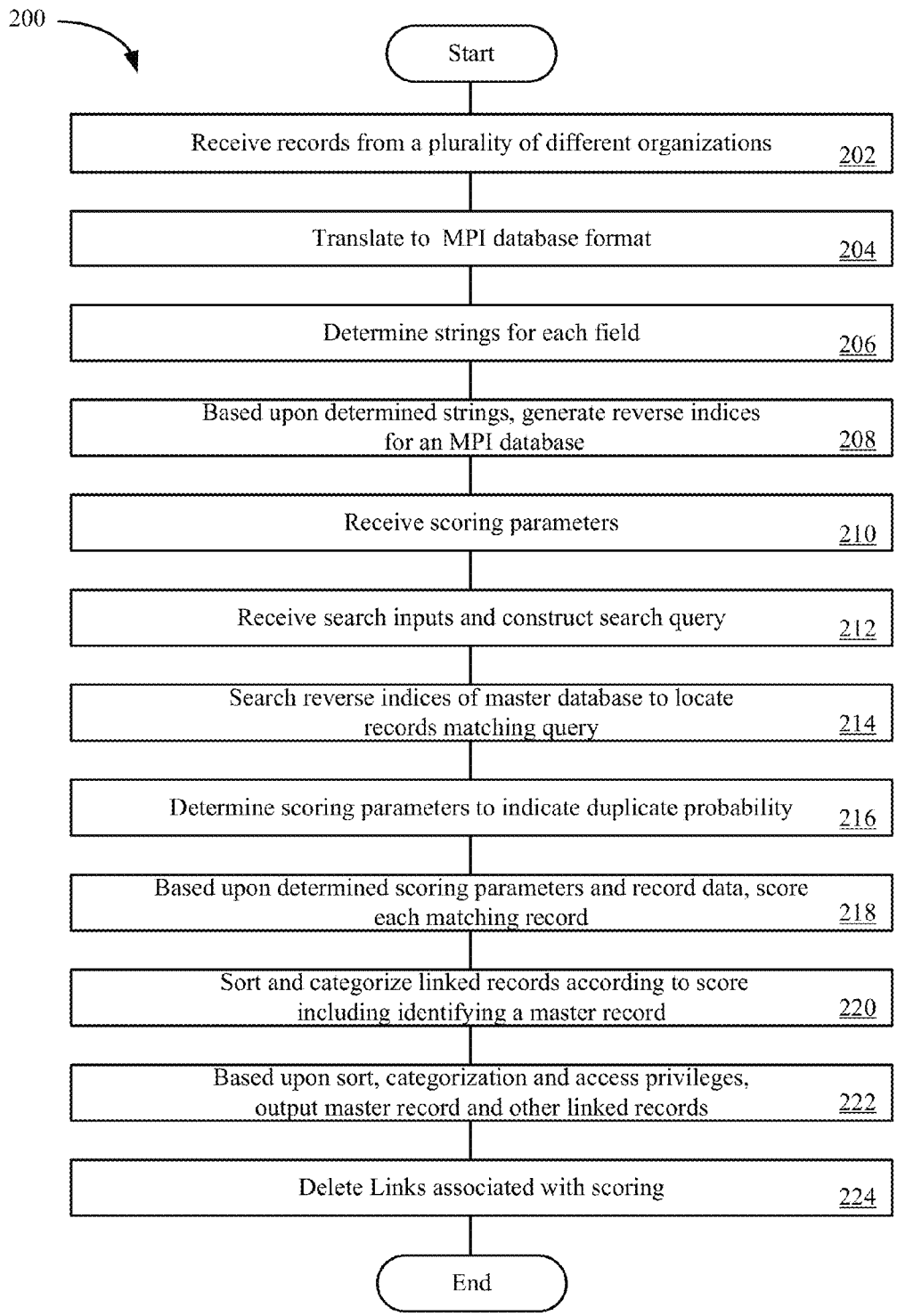
FIG. 4 is a flow chart of a method of managing an MPI system including an MPI database with inverted indices and probabilistic duplicate scoring in accordance with the described embodiments.

With respect to FIG. 4, a method of managing an MPI system including an MPI database with inverted indices and probabilistic duplicate scoring is discussed. The method includes steps related to: 1) creating and querying the MPI database and 2) scoring and organizing search results associated with duplicate records. With respect to FIG. 5, a method of updating an MPI database using inverted indices is described. With respect to FIG. 6, a method of adjusting duplicate scoring in an MPI system having an MPI database using inverted indices is discussed. In one embodiment, the duplicate scoring can be adjusted to account for systematic errors occurring in a dataset.

Next, details of a MPI system interface are described. For illustration, a number of potential states of the MPI system interface are presented. In particular, with respect to FIG. 7, a MPI system interface state including data comparisons of duplicate records is discussed. With respect to FIG. 8, a MPI system interface in a state allowing modification of a data field associated with a number of duplicate records is described. With respect to FIG. 9, a state of a MPI system interface showing a user dashboard is discussed. With respect to FIG. 10, a state of a MPI system interface showing merge history information is described. With respect to FIG. 11, a state of a MPI system interface showing audit trail information resulting from accessing and/or modifying the MPI database is discussed. Finally, with respect to FIG. 12, a method of modifying duplicate records via an MPI system interface is described.

Inverted Index Database Structure and MPI Management System Overview

In this section, methods and apparatus for constructing a MPI database using an inverted index formulation and a system which leverages this formulation are described. FIG. 1 is a block diagram of healthcare information 10 managed in a healthcare organization. The healthcare information can include Electronic Protected Healthcare information. Electronic protected health information (ePHI) refers to any protected health information (PHI) that is covered under Health Insurance Portability and Accountability Act of 1996 (HIPAA) security regulations which is produced, saved, transferred or received in an electronic form. The law enumerates eighteen specific types of electronic protected health information, including patient names, addresses, Social Security numbers, email addresses, fingerprints or photographic images, among others. In addition, any past medical records or payment information is also subject to the same degree of privacy protection.

Regardless of the type of electronic device—PC, tablet PC or smartphone—used to access electronic protected health information, users must abide by HIPAA security rule guidelines when handling both information at rest and that which is being transferred electronically, via email or file transfer. To comply with the security guidelines, ePHI data is typically stored in an encrypted format. Further, any transfers of information, such as over a wide area or local area network, is performed using encryption techniques. For example, for transfers over the Internet involving a client and a server, such as a remote client accessing information from an MPI database, techniques like Secure Socket Layer (SSL) can be utilized.

In the embodiments described herein, some portion of the information stored in the MPI database is likely to be considered ePHI. Thus, records in the MPI database and inverted indices associated with the MPI database can be encrypted when at rest. When the MPI database is accessed, such as when the database is queried for duplicate records, all or a portion of the database and inverted indices can be unencrypted. Then, information associated with a search, retrieved from the MPI database, can be sent in an encrypted manner over the network.

In one embodiment, the records and inverted indices are associated with a first data store 12. Each record in the data store 12, such as records 20, 22 and 24 can include a number of fields where each field can have one or more values. One embodiment of a healthcare record is shown below with respect to Table 1.

TABLE 1

Example of Field included in a patient record

| No | Name | Field Type | Description |
|---|---|---|---|
| 1 | facilityId | Single value | Identifier domain, such as a practice code or grouping code |
| 2 | internalPatientId | Single value | Unique ID for record in the MPI database |
| 3 | facilityLocalId | Multi-valued | Medical record numbers and other IDs assigned by a facility (e.g., lab, practice group, etc.) |
| 4 | facilityLocalIdSrc | Multi-valued | Facility local ID source (Identifier for facility) |
| 5 | personalId | Multi-valued | Patient's driver's license information, military ID information, passport information, green card information, etc. |
| 6 | personalIdType | Multi-valued | Personal Id Type - Driver's license, Military IDs, Passport information, Green Card, etc. |
| 7 | personalIdValidity | Multi-valued | Flag to indicate whether the personal Id is active/inactive (e.g., valid or expired driver's license) |
| 8 | firstName | Single value | Patient's first name |
| 9 | lastName | Multi-valued | Patient's last name |
| 10 | middleName | Single value | Patient's middle name |
| 11 | nickName | Single value | Patient's nick name |
| 12 | Sex | Single value | Sex (M, F, Male, Female) |
| 13 | dateOfBirth | Single value | Date of birth |
| 14 | SSN | Single value | Social security number |
| 15 | address 1 | Multi-valued | Address 1 |
| 16 | address 2 | Multi-valued | Address 2 |
| 17 | City | Multi-valued | City |
| 18 | State | Multi-valued | State |
| 19 | addressValidity | Multi-valued | Flag to indicate whether the address is active/inactive |
| 20 | postalCode | Multi-valued | Postal code |
| 21 | Phone | Multi-valued | Patient's phone numbers |

TABLE 1-continued

Example of Field included in a patient record

| No | Name | Field Type | Description |
|---|---|---|---|
| 22 | PhoneType | Multi-valued | Phone Type (Home, business, mobile, fax) |
| 23 | PhoneValidity | Multi-valued | Flag to indicate whether the phone number is active/inactive |
| 24 | Email | Multi-valued | Email |
| 25 | EmailValidity | Multi-valued | Flag to indicate whether the Email is active/inactive |
| 26 | Race | Single value | Race |
| 27 | RecSrcId | Single value | Record Source Id |
| 28 | timestamp | Single value | Time when this patient record was added or updated |

In the example of table 1, a record can include twenty eight fields where many of the fields are allowed to have multiple values. For example, multiple addresses, phone numbers and email addresses can be stored in a single record. The number of fields and the selection of which fields are multivalued can be varied and the example described above with respect to Table 1 is provided for the purposes of illustration only and is not meant to be limiting.

In operation, the level of completeness and the amount of data can vary from record to record and can change over time. For example, in a first record a number of fields may be blank while in a second record some information may be stored for all the fields. As another example, a first record can have five values for an Email, three values for an address and two values for a phone number while a second record can have zero values for an Email, one value for an address and three values for a phone number.

An inverted index can be constructed for each field. The inverted index can include a list of strings and then a pointer to which records include the string in the field. The strings are values which appear in the healthcare records which have been indexed. Typically, the pointer can point to the unique identifier in the MPI database associated with a healthcare record. Each string can have a pointer to one or more healthcare records as the same string can appear in multiple healthcare records. In a search query, terms in the query can be matched to the strings in the query allowing a search to be quickly carried out over all the healthcare records in the MPI database.

As an example, under the field "sex," a few strings can be the letter "M," and the words, "Man" or "Male." For each of these strings, the inverted index can list the healthcare records that include these values in the field associated with sex. For example, records 1, 5, 5000 and 1,000,000 can include "M," records 2, 6, 5001 and 1,000,001 can include "Man" and records 3, 7, 5002 and 1,000,002 can include "Male." Thus, when a query is performed, which identifies a particular value or some combination of values in a field, all the healthcare records in the MPI database which contain the values can be quickly identified. In addition to the record identifier in the data store 12, the data block on the disk or other memory device where the record is available can also be stored for faster retrieval, which is not shown in the example above.

In FIG. 1, inverted indices 26, 28 and 30, which are associated with fields, one, two and "M" each include values (search strings) one to "N" which can each point to one or more healthcare records which range from one to "P" where "P" is the number of unique healthcare records in the MPI database. Each value in the inverted index can point to at least one healthcare record. A particular value can be repeated in a number of healthcare records. Thus, the particular value can be associated with more than one record. For example, the last name, "Smith" may appear in five healthcare records. Therefore, the value "Smith" in the inverted index for the last name field can point to the five healthcare records including the last name "Smith."

The fields range in values from 1 to "M." In the example above from table 1, "M" is equal to twenty eight. Thus, a healthcare record can be configured to receive twenty eight different types of information. As described above, for each field, one or more values can be received. For example, the healthcare record described in Table 1 can be configured to receive multiple phone numbers in the phone number field.

The possible number strings range in value from 1 to "N" where a value of "N" can vary from field to field. For example, the number of possible strings associated with a first name may be greater than the number of possible strings associated with gender. The strings correspond to the values appearing in the fields of the healthcare records.

As new healthcare records are added or existing healthcare records are modified. The string values appearing in the inverted index can change. In particular, new string values can be added or existing string values can be deleted. For example, when a patient with a unique last name which has not previously appeared in the MPI database is registered, the unique last name can be added as a new string value to the inverted index with a pointer to the healthcare record in which the unique last name appears. If the healthcare record including the unique last name is subsequently deleted from the MPI database, then the string value associated with the unique last name can be deleted from the inverted index.

The unique records in the MPI database vary from a range of 1 to "P." In various embodiments, the number of uniquely identified records can be up to a thousand, up to ten thousand, up to one hundred thousand, up to one million or greater than a million. In one embodiment, at least one million uniquely identified records are included in the MPI database. As described below, some records can be identified as duplicates in the MPI database. However, unless the records are merged into a single record, the duplicate records can still be uniquely identified records.

A string value in the inverted index can correspond to some combination of upper case letters, lower case letters, numbers, characters, symbols, etc. which appear in one of the fields of a healthcare record. The strings don't have to correspond to expected values of the field and can include typos and other mistakes which may appear in a record. For example, string values for gender in an inverted index might include "M," "Male," "Mail," "Man," "guy," "boy," "MALE,"

"m," "F," "Female," "Finale," "Feemail," "Feemale," "femail," "FEMALE," "f," "Woman," "W," "girl," and "lady."

The string values can be determined from indexing the healthcare records in the MPI database. The indexing can involve determining the unique string values which appear in each of the different fields of the healthcare records. In particular embodiments, an inverted index can be generated for all or a portion of the fields in the healthcare record format. For instance, if searches are not performed on a particular field in the healthcare record format, then an inverted index may not be generated for the unsearched field.

As another example, strings for a person's age, like the age of forty, might appear as "40," "forty," "04," "$0," "$)," "4(," or "400" where the inverted index includes pointers to the records in which they appear. For example, the numbers can be reversed as in "04" or a shift key can be held down when entering a value, such as "$" instead of "4" or an extra character might be added, such as "400" which includes an extra zero. These strings represent different ways of entering the age forty or typos that might occur when entering the age which may have occurred in records in the MPI database and are hence captured in the inverted index. Similar errors might occur when entering values for an area code in a phone number.

Many systems don't include checks for limiting entered values to expected values. Further, the expected values can be different from system to system. For example, one system might expect "F," and "M" as an expected value for gender while a second system may expect "Female" or "Male," When records from systems with different expected values or without error checking are combined, the differences in expected values or typos can lead to duplicate records for the same person.

Query structures can be formulated for capturing certain related typos or other related ways of entering information, which may not conform to an expected value, in a duplicate detection scheme. For example, a query for "40" above may also search for "04" as a potential match or "400" as a potential match. When scoring is performed, the related information identified in the query may be given a score which is the same or different than an exact match. For example, for a query on the value "40," a record containing "40" or "400" can be scored the same or "40" might be given one score while the value "400" might be given some score greater than zero but not as large as records which exactly include the character string "40."

As will be described below, multiple types of searches can be carried out on a field to try to account for different ways in which data referring to the same concept can be entered, i.e., the format of the data entry is different but the quantity to which the data represents is the same. For example, the concept of street in an address can be entered as "Street," "Str" or "Ave." One aspect of duplicate probability scoring is attempting to determine whether various differences between information stored in two similar records is different because the records refer to different individuals or is result from pieces of comparable information being expressed in a different way, such as entered in a different accepted formats or as result of a typographically errors during data entry. Further details of querying and scoring for duplicate matches are described below with respect to FIG. 2.

In some embodiments, certain information can be stored in a field of a record with multiple values which account for some of the variations and/or typos that commonly occur when representing the information associated with field. For example, a first name in a record can be stored along with synonym and phonetic spellings of the first name which are indexed as part of the inverted index. The additional information, such as synonyms can be added to the field in the record and hence the inverted index to enable better duplicate detection. For example, when the name "Gray" appears in a record, the names, "Grey" or "Grae" can also be added to the record and then indexed for duplicate detection purposes. As another example, if the name, "John,Gray" appears in a first name field, this string might be split, stored and indexed as "John, Gray," "John" and "Gray" for duplicate detection purposes. As yet another example, the phone number "510-555-1234" might be stored as "5105551234," "510," and "5551234" for duplicate detection purposes.

As records are accessed, updated and merged via the MPI management system, an audit trail and update/merge history can be generated. The audit trail can record a "who, what and when," i.e., who accessed the MPI database, what did they do to a record in the database and when did they do it. An example of MPI management system interface in a state with audit trail information is described below in more detail with respect to FIG. 11.

The update/merge history function can allow a history of a record to be tracked such that a state of a healthcare record at different times is maintained. Using the healthcare record history, it may be to reverse changes to the healthcare to revert a healthcare record to a previous state. For example, two records can be identified as duplicates and merged into a first healthcare record while the second healthcare record is deleted. A MPI management system interface can be configured to show when the merge took place and allow the action to be reversed. For example, the two records merged into a single record can be restored to their states prior to the merge. Thus, one record can be undeleted and the changes to a second which occurred during the merge can be reversed. As another example, if a healthcare record is updated with new information. The MPI management system interface can be configured to show when the update took place, some details about the update, such as what fields where updated and provide the capability to reverse the update to reverse the record its state just prior to the update.

Over time, a record may go through a sequence of updates and merges that change the information contained in the record and may cause the record to be deleted when it is identified as a duplicate and merged with another record. In one embodiment, the MPI management system interface can be configured to display the historical changes to the record over time and provide the capability to revert the record and/or associated records (e.g., a record merged into another record and then deleted) to a state at previous time prior to a historical action taking place. An example of MPI management system interface state configured to provide these capabilities is discussed in more detail with respect to FIG. 10.

In one embodiment, the audit trail and merge history information are stored in a second data store 14 separate from the first data store 12 which includes the healthcare records and the inverted indices. This approach minimizes the amount of data stored in the first data store 14, which can speed up the searching process. In an alternate embodiment, the first and second data store can be combined into a single data store.

A number of applications, such as the MPI management system interface described below with respect to FIGS. 7-12, can be configured to leverage the data stored in the first data store 12 and the second data store 14. Application data 18 can be associated with the applications. For example, one type of application data can be user preferences. User preferences may include one or more user-selectable settings for an application, such as settings for the MPI management system interface. In another example, the user preferences may include specifically constructed search queries which an individual or organization frequently used. In yet another example, the user preferences may include unique duplicate matching scoring algorithms which are particular to an organization.

In one embodiment, the healthcare information 10 can be from multiple healthcare organizations where individuals in a healthcare organization may only be able to view patient information from healthcare records associated with patients in their healthcare organization. Further, within a healthcare organization, access to certain patient records may be limited to a subset of departments within an organization. The access control settings can be used to specify which records an individual is allowed to access within the MPI database where only a system operator may be able to see all of the healthcare records within the MPI database.

In one embodiment, the application data 18 can be stored in a third data store 16 separate from the first data store 12 and the second data store 14. In another embodiment, the second data store 14 and the third data store 16 can combined into a single data store. In yet another embodiment, the first, second and third data stores can be combined into a single data store.

MPI Database Management Including Querying and Duplicate Scoring

Figure 2:
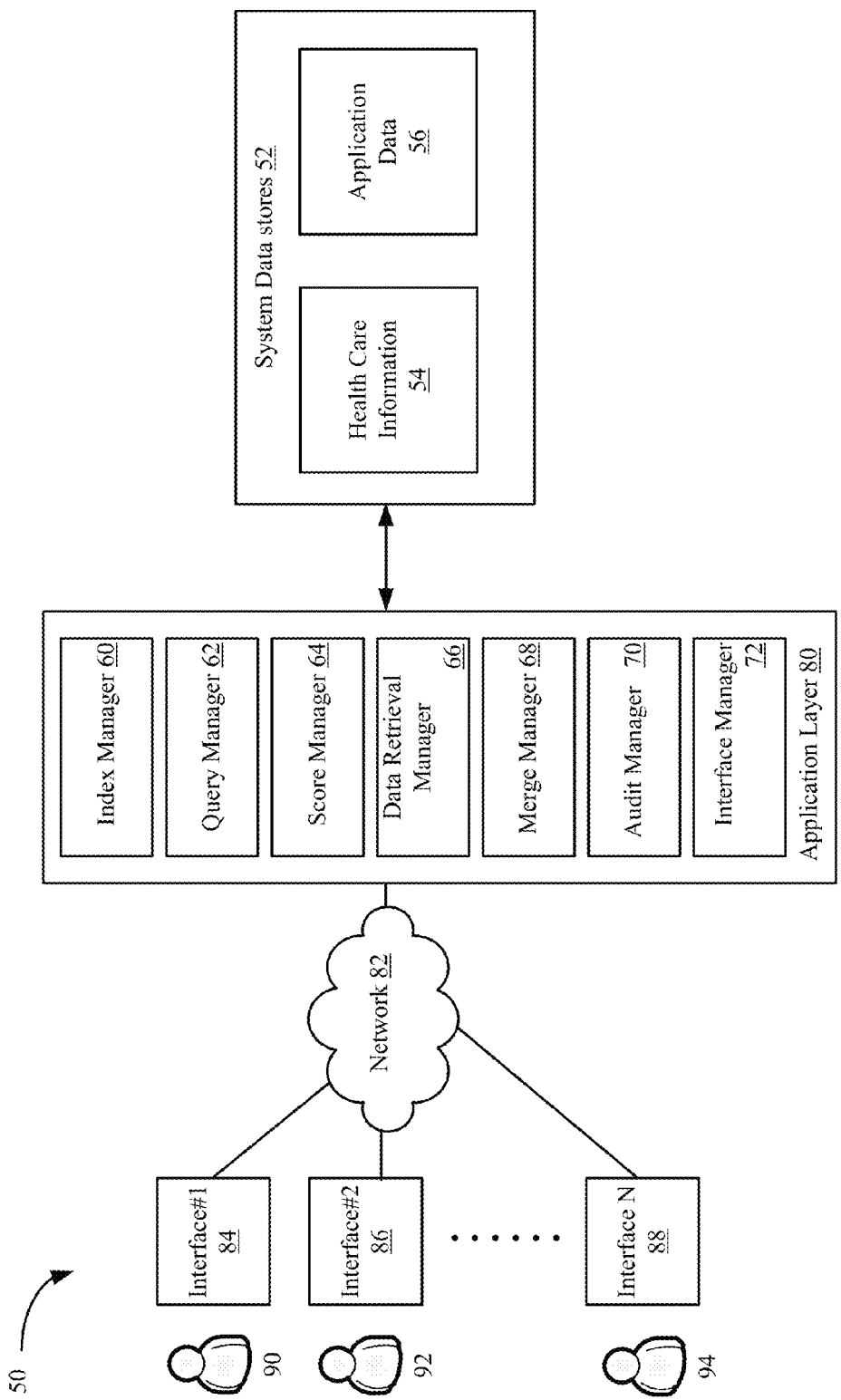
FIG. 2 is a block diagram of an MPI management system in accordance with the described embodiments.

Next details of an MPI management system are described including querying and duplicate scoring of the inverted indices described above with respect to FIG. 1. FIG. 2 is a block diagram of an MPI management system 50. The MPI management system 50 can include an application layer 80 which includes a number of applications which utilize system data stores 52. The system data stores 52 can include the healthcare records including patient healthcare information 54, application data 56 and other types of data previously described with respect to FIG. 1.

In one embodiment, the application layer 80 can include an index manager 60, a query manager 62, a score manager 64, a data retrieval manager 66, a merge manager 68, an audit manager 70 and an interface manager 72. The index manager 60 can be configured to generate and update the inverted indices associated with the system data stores 52. Each time a record is merged, deleted, updated or a new record is added to the system, such as via a merging of systems with legacy records or registration of a new patient, the index manager 60 can be configured to update an inverted indices associated with the MPI database to account for new values appearing in the healthcare records or new records in which an existing value appears.

As an example, when a new patient is added to the MPI database, their first name and last name can be provided. The index manager 60 can be configured to determine if the last name exists as value in the inverted index for the last name field. When the last name already exists, a pointer to the new record including the last name can be associated with the string or strings representing the last name and the index can be updated. When the last name doesn't exist, a new string or strings can be added to the inverted index which represents the last name and a pointer can be associated with the string which points to the newly added healthcare record. Similar operations can be performed on the inverted index for the first name field as well as any other fields of the healthcare record which are indexed.

When the newly added record is subsequently updated, the inverted indices can be updated. For example, if the new record didn't include a phone number when the patient was initial registered and a phone number is subsequently added or the new record included a first phone number but then an additional phone number is added, then the inverted index associated with the phone number field can be updated. The update can involve adding a string value with the newly added phone number and adding a pointer to the string value which points to the updated healthcare record.

The query manager 62 can perform functions related to querying. The functions associated with querying can include searching the inverted indices in accordance with specified syntax in a query structure. If desired, the searches can be customized for each field so that it goes beyond the information which is specified in the query. For example, if a query specified search for the number "40" in a particular field. The query logic 62 can be configured to search for only the string "40" or can be configured to search for the string "40" and typographical variations of the string "40." The default option can be to search only for only the string "40," i.e., an exact match, and the user may have to specify instructions to also search for common typographical errors. As another example, the default option may be to search for the string and any common typographical errors and the user may not have to instruct the system to search for the common typographical errors.

The default query structures can be selected to best find duplicate records. In some embodiments, the default query structures can be organization specific to account for data patterns associated with the records of the organization. For example, if an organization, commonly misspells names in a certain way, then the queries for the organization can be configured to account for these errors. A few examples of query structures and syntax which can be used with the data record fields described above with respect FIG. 1 and Table 1 are described as follows. These examples are provided for the purposes of illustration only and are not meant to be limiting.

FacilityId is one of the fields identified in Table 1. If facilityId is present in input, then it can be appended to the query with a (+) operator. The (+) operator or mandatory operator requires that a term after the plus symbol exist somewhere in the field of a single record. For example, when input comes with facilityId: "RC01". The query "+facilityId:RC01" can be generated. The "+" symbol indicates RC01 needs to be in the facilityID field for the healthcare record as a whole to be identified as a match.

In a case of a search (not search and register), multiple FacilityIds can be received as input as part of a search of the FacilityIds field. In this case at least one of them may need to be matched mandatorily. For example, when input comes with FacilityIds: ["RC01", "RC02"], the query which may be constructed is "+(facilityId:RC01 facilityId:RC02)." In this example, at least one of "RC01" or "RC02" needs to appear in the facilityId field of the record for the healthcare record as a whole to be considered a match to the query. Using inverted index for the facilityId field, the system searches for the strings "RC01" or "RC02" over all of the healthcare records in the MPI database. When the strings are found, then any pointers to records associated with the strings can be identified.

Sex is another field in Table 1. When sex field is specified in the input query and if it is either "M" or "F" (case insensitive), then it can be appended it to the query with a weightage of sexExact score. The weightage as will be discussed in more detail below is how much will a match of this information in the sex field contribute to a duplicate probability score. The term "U" (undefined), which provides no weightage to the score, can be appended to the query. This query can again be put as mandatory (+). As an example, when input comes with sex: "m," a query, "+(sex:m^50 sex:u)" can be constructed.

Race is a field in Table 1. The race field can be handled similar to the sex field. For example, when input comes with race: "Asian," a query, "+(race:asian^50 race:u)" can be constructed.

FirstName is a field in Table 1. In one embodiment, the first name can be matched mandatorily. The firstName can be matched phonetically as well as exactly. A separate field called, firstNamePhonetic, can be provided for matching a name, phonetically. As described above, a first name can be converted to a phonetic representation and stored to a record. As example, when input comes with firstName: "Muthu," a query, "+(firstName:Muthu^1500 firstNamePhonetic: Muthu^700)" can be constructed. In this example, a value of fifteen hundred is contributed to a duplicate probability score if there is an exact match and a value of seven hundred is contributed if there is a phonetic match. Different weighting values can be used and these are provided for the purposes of illustration only and are not meant to be limiting.

LastName is a field in Table 1. Last name can be handled similar to first name. In one embodiment, however, a match may be optional, i.e. no + operator in the query. Thus, the result can include healthcare records in which last name is a mismatch of the search query. Last name mismatches can be given a lower priority such that the healthcare including the mismatches appear toward the end of list of healthcare records returned for a particular query. In one embodiment, as described above, synonym matching like phonetic matching can also be applied in a query schema. As an example, when input comes with lastName: "Smith" a query, such as "lastName:Smith^1500 lastNamePhonetic:Smith^700 lastNameSynonym^700." In this example, a higher score of fifteen hundred is given to an exact match as compared to a phonetic or synonym match. In alternate embodiments, one or a combination of the "lastName," "LastNamePhonetic" or "LastNameSynonym" fields can be made as mandatory in a search query construction.

MiddleName is a field in Table 1. Middle name can be handled similarly to the last name. In one embodiment, synonym matching can be applied as per analyzers defined in the schema. As an example, when input comes with middleName:Edward, a query "middleName:Edward^300 middleNamePhonetic:Edward^150" can be constructed. In this example, the contribution to a score for a middle name string match is three hundred and for a phonetic match is one hundred fifty. The value contributed to a score for a middle name phonetic name is less than the exact spelling match which is less than the values contributed to a duplicate probability score for a first name or a last name match.

DateOfBirth is a field in Table 1. In one embodiment, the date of birth can be mandatorily matched. However, a single digit mismatch can be allowed. In one embodiment, a fuzzy logic match criteria with a weightage of 0.8 can be used with a search platform to perform the search. The weightage number can be derived empirically. As an example, when input comes with dateOfBirth: "19400310", a query of "+dateOfBirth:19400310~0.8^300" can be constructed where a match, including a digit mismatch, contributes a value of three hundred to a score. Queries involving multiple digit mismatches are possible and the example of a single digit mismatch is provided for the purposes of illustration only.

Email is a field in Table 1. In one embodiment, Email can be matched as an optional field. For example, when input comes with email: "test@example.com," a query, such as "email:test@example.com^300," can be constructed. In this example, a score of three hundred is contributed to a match.

SSN, which is the social security number, is a field in Table 1. In one embodiment, SSN can be matched optionally. In another embodiment, it can be matched exactly as well as the last four characters. For example, when input comes with SSN: "123456789" a query of "ssn:123456789 ssnLastFour: 6789" can be constructed. In this example, values to contribute to a score are not specified. However, different values can be specified for a total match as well as a match of the last four numbers.

In application, the system can attempt to determine whether there are any exact matches and any last four digit matches within the healthcare records of the MPI database. A healthcare record which is an exact match for the whole number will also be a last four digit match. However, for the purposes determining a duplicate probability score for a single record, the system can be configured to only use the contribution from the exact match of the whole number and not the contributions from both the whole number match and the last four digits of the number match.

Address1 and Address2 are fields in Table 1. Both fields can be multi-valued. For example, Address1 can include a current address and a series of previous addresses. In one embodiment, Address1 can be matched optionally. Further, a phrase query match can be used. For example, when input is received via the interface, with address1: "2730 CORPREW AVE APT A," a query of "address1:"2730 CORPREW AVE APT A "^100" can be constructed. In this example, a match contributes a value of one hundred to a probabilistic matching score. Address2 can be matched optionally just like Address1. For example, when input comes with address2: "APT A," a query of "address2:"APT A "^100" can be constructed. In this example, a match also contributes a value of one hundred to a probabilistic matching score.

State (as in one of the fifty states in the United States of America) is a field in Table 1. In one embodiment, state can be matched optionally. Quotes can be added around the input so that the initials for the state Oregon, "OR," is not confused with the "or" search operator. As an example, when input comes with state: "VA," a query "state:"VA "^50" can be constructed. In this example, a value of fifty is contributed to the score for a matching state in a healthcare record. Other regional identifiers which may be specific to a country in which the MPI system is deployed can be utilized and "state in the United States" is provided for the purposes of illustration only. For example, in Canada, province can be used as a regional identifier.

PostalCode is a field in Table 1. Postal code can be matched optionally. As an example, when input comes with postalCode: "235044047", a query can be constructed of "postalCode: "235044047"^70." The value seventy can be attributed to a score when a match in a record is detected.

Phone is a field in Table 1. Input can come with multiple phone numbers. In one embodiment, all of the received numbers can be matched optionally. As example, when input comes with phone numbers: ["7048572888", "80481728323"], a query of "phones:7048572888^300 phones:80481728323^300" can be constructed. In this example, a value of three hundred is added to a probabilistic matching score when a correct match is detected for either phone number.

In one embodiment, a maximum of three hundred is contributed to a duplicate probability no matter how many phone numbers are matched, i.e., a maximum contribution value is set for phone number matches. In another embodiment, three hundred can be contributed for each match up to some maximum value or without a maximum value. In yet another embodiment, a first value can be contributed for the first match and a second value can be contributed to a second match. In some instances, the contribution to the duplicate probability score can be less for the second match as compared to the first match. This type of scoring can be used for any field which is multi-valued and hence multiple matches are possible.

Facility Local Id is a field in Table 1. Facility local Id can refer to identification information associated with a facility or practice within an organization, such as a lab or a practice specialty. In one embodiment, input can be received with multiple facility local id values. In another embodiment, all of them are matched optionally. As an example, when input comes with FacilityIds: ["1234", "5678"], a query of "facilityLocalId:1234^300 facilityLocalId:5678^300" can be constructed. Values of three hundred are contributed to a probabilistic matching score when a match is detected. In yet other embodiments, which is the case for any of the fields, a field can be designated as mandatory and a "+" operator can be used in the query construction for the field.

PersonalId is a field in Table 1. Personal identification can refer to various forms of identification, which are issued by various entities, such as but not limited to a government entity. For example, a driver's license issued by a state government, a passport issued by a country and a student ID issued by a college are three forms of personal identification. In one embodiment, input can be received with multiple personal id values specified. All or a portion of the IDs can be matched optionally. For example, when input comes with personalIds: ["abc", "pqr"], a query can be constructed as "personalId:abc^300 personalId:pqr^300." In this example, a value of three hundred is assigned to a probabilistic matching score when a match is detected.

In general, for each of the fields received as input for a query, a query fragment can be constructed for the field as mentioned above. All of the received fields can be concatenated to create a single combined query. The single combined query can be passed to a search engine, such as Solr™, and a search of the inverted indices can be carried out according to the specified query over all of the records in the MPI database each time a search query is performed. A duplicate probability score can be determined for one or more healthcare records which satisfy the constraints associated with the query. Then, records can be output, such as via a user interface, in accordance with the determined duplicate probability score.

Contributions to a duplicate probability score can be determined on a field by field basis. For particular healthcare record, a score can be based upon matches in one or more fields of the particular healthcare record according to the particular query. Thus, a determination of a score for the particular healthcare record may involve combining the contribution to the score from a number of matches in different fields of the healthcare records. For a particular query, the number of fields which are matched and the particular fields which are matched can vary from healthcare record to healthcare record.

For example for a first search query, a particular healthcare record may match the search query in three different field while in a second search query the particular healthcare record may match the query in four different fields. The matching fields from first search query and the second search query may or not overlap each other and the amount of overlap can vary. For instance, three of the fields matched may overlap or a single field may overlap between the two search queries. Thus, the duplicate probability score associated with the same healthcare record may vary depending on how the search query is formulated.

In addition, it is easy to change to weights associated with a search query, i.e., the contribution a match of a field contributes to a duplicate probability score because the method doesn't require possible duplicate relationships between healthcare records to be maintained. Thus, duplicate probability scores can vary from query to query because the weighting factors have been changed. In one embodiment, the system can be configured to allow a user to vary the weights contributed to a duplicate probability score resulting from matches in one or more different fields in a search query.

Returning to FIG. 2, a score manager 64 can keep track of the values contributed to matches in a query. These values can be changed over time including in real-time and can vary from organization to organization and data set to data set. A number of contribution values are described above for duplicate probability score formulation. However, these are provided for the purposes of illustration only and are not meant to be limiting.

In addition to keeping track of contribution values (can also be referred to as weights) used to determine a duplicate probability score, the scoring manager 64 can be configured to compare a determined duplicate probability score to a specified scale and categorize scored healthcare records according to the scale. For example, records with a score above a first threshold value can be categorized as a strong match, while records with a score between the first threshold value and a second threshold value can be considered a likely match and scores below the second threshold value can be a weak match. In various embodiments, the number of categories and thresholds for being placed in each category can be varied. Additional details of duplicate probability scoring are described below with respect to FIG. 3.

The data retrieval manager 66 can be configured to retrieve records which were identified and scored via a search query. In one embodiment, a particular record may not be retrieved until the system receives an input indicating that a user wants to view details of the record, such as via an interface. This feature can reduce unneeded database retrieval operations and decryption operations.

The merge manager 68 can be configured to track changes to records, such as via an update, merge or deletion. The changes can be stored such that the changes are reversible and history of record changes can be viewed. For example, the merge manager 68 may be configured to output information associated with a record before and after each of a series updates and indicate/highlight the changes that occurred at each event. As described above with respect to FIG. 1, this information can be stored in a data store separate from the main data store including the patient records. An example of an interface state configured to generate some of the merge features is described below with respect to FIG. 10.

The audit manager 72 can be configured to keep track of information, such as but not limited to 1) who is accessing the system data stores, such as 52, 2) what was done during the access, 3) when it was done and 4) from what location the actions were performed. For example, the audit trail can track that a particular person logged into to the system, performed a particular query and viewed a number of records during a particular time period from a particular network node and/or device node on a network. An example of information associated with an audit trail and an associated interface component is described in more detail with respect to FIG. 11.

The interface manager 72 can be configured to present information and configuration features associated with the other managers, such as but not limited to the index manager 60, query manager 62, score manager 64, data retrieval manager 66, merge manager 68, audit manager 70, to system users. As different users access the system 50, the interface manager 72 can be configured to generate a number of different interfaces where the number varies over time.

Depending on the access privileges of a particular user, which may be verified via a reception of login credentials or other security information, a user may be granted an interface with more or less features and more or less access to the healthcare records within the various data stores 52. For example, the data stores 52 can include healthcare information associated with multiple organizations and access to the healthcare records for a particular individual may be limited to patients within their organization. Whereas, a system operator may be have access to all of the healthcare records in the database. In FIG. 2, users 90, 92, 94 are accessing the system via interfaces 84, 86 and 88 over network 82.

In the system of FIG. 2, the application layer 80, associated applications and system data stores 52 can be provided on one or more servers each including one or more processors, memory and networks interfaces. In one embodiment, the servers can be virtual devices instantiated in a cloud configuration. In some embodiments, some of the functions in the application layer can be generated on client side device. In general, the functions performed by the different applications can be distributed between client side device and host device where assignment of particular functions to a host side or client side can vary from embodiment to embodiment. Further on the host side, functions can be distributed across various host devices which work in conjunction with one another to provide an application.

Figure 3:
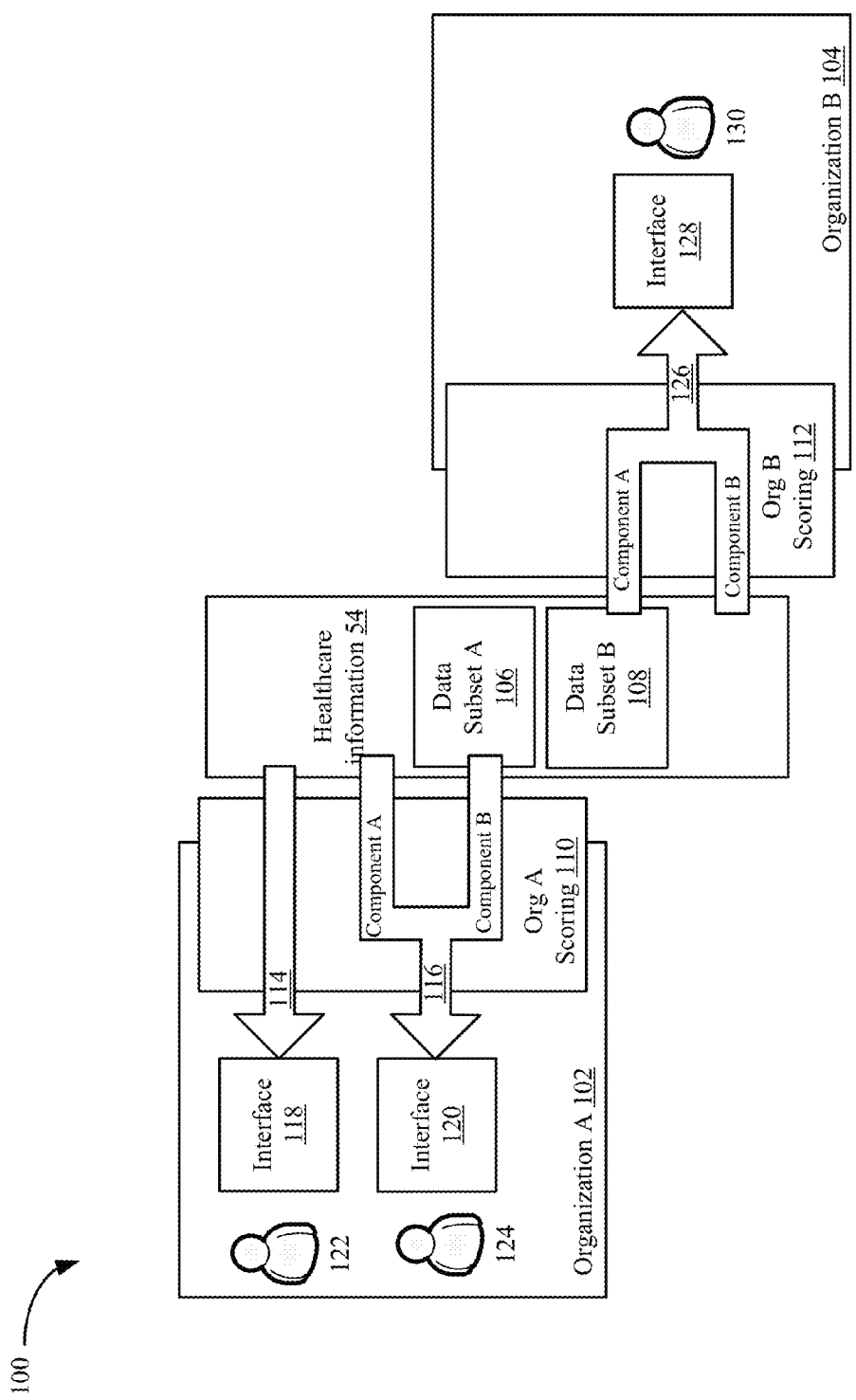
FIG. 3 is block diagram showing organization specific scoring within the MPI management system in accordance with the described embodiments.

Next additional details of scoring are discussed. FIG. 3 is block diagram showing organization specific scoring within the MPI management system 100. As described above, inverted indices can be generated for a database including healthcare information, such as 54. The healthcare information can include patient healthcare records where some of the records may be duplicates, i.e., records associated with same person. The system can be configured to allow a user to input search terms which allow the healthcare records to be searched and duplicate records to be identified.

Based upon the input search terms, the system can construct a query to search the inverted indices for records which match the query. Then, the records identified by the search query can be scored to reflect how likely the records are duplicates. The scoring can be based upon assigned weights for matching different types of information in the healthcare records. For example, an exact name match can be given a first contribution value to a duplicate probability score while a match to an address can be given a second contribution value to a duplicate probability score.

Via an interface of some type, healthcare information associated with matching records can be output to a user which implemented the search query over the MPI database. In one embodiment, the search results presented via the interface can be sorted according to how much information from the query is matched. For example, a record which includes information matching a first name, last name, address and phone number specified in a query may be given a higher duplicate probability score and presented ahead of a record which matches only the first name and the last name and hence has a lower duplicate probability score.

In one embodiment, a duplicate probability score can be formulated by assigning different values to matches of information associated with a healthcare record. As described above, all or portion of the fields can be assigned values which contribute to a score. An example of such a scoring system is described below with respect to Table 2, which includes a name of a type of information to be matched, a score assigned to the match and a description of the information which is matched.

TABLE 2

Scoring System and Weights

| Name | Score | Description |
|---|---|---|
| internalPatientId | 4000 | Unique ID for MPI database |
| facilityLocalId | 300 | Medical record numbers and other IDs assigned by a facility (e.g., lab, practice group, etc.) |
| personalId | 300 | Patient's driver's license information, military ID information, passport information, green card information, etc. |
| firstNameSynonym | 1500 | Match to a synonym of patient's first name |
| firstNamePhoenetic | 700 | Match to a phonetic spelling of name |
| lastNameExact | [1500, 1000] | Exact match to patient's last name |
| lastNamePhonetic | [700, 500] | Match to phonetic spelling of name |
| lastNameSingleCharacter | [1400, 900] | Match to last name allowing for single character mismatch (one or more characters mismatches can be scored, i.e., two letter mismatches, etc.) |
| middleNameSynonym | 300 | Match to synonym of patient's middle name |
| middleNamePhonetic | 150 | Match to synonym of patients middle name |
| middleNameSingleCharacter | 300 | Match to middle name off by at most one character |
| SexExact | 50 | Sex (M, F, Male, Female) |
| dateOfBirthExact | 1200 | Exact match to date of birth |
| dateOfBirthSingleDigitMismatch | 300 | Match of date of birth with one digit mismatch |
| SSNExact | 300 | Exact match to social security number |
| SSNLastFour | 150 | Match to last four numbers of social security number |

TABLE 2-continued

Scoring System and Weights

| Name | Score | Description |
| --- | --- | --- |
| address 1 | 100 | Address 1 |
| address 2 | 100 | Address 2 |
| City | 45 | City |
| State | 50 | State |
| postalCode | 70 | Postal code |
| Phone | 300 | Patient's phone numbers |
| EmailExact | 300 | Exact match to email address |
| RaceExact | 50 | Exact match to race |
| SexExact | 50 | Exact match to sex |

In the example above, a score of fourth thousand and above can be considered a match. A score of three thousand to fourth thousand can be considered a weak match. More refined scales, i.e., more thresholds, can be formulated and these are provided for the purposes of illustration only.

As can be seen in Table 2, matches to different types of information, as defined by the fields in the healthcare records, can contribute more to a score than other types of information. For instance, if the internal patient ID number is matched, the record is considered a match independent of whether any other additional information in a healthcare record is matched.

In the example above, one or more components or combinations of the score may be considered mandatory in a match. For information designated as mandatory, the record can be required to have the mandatory information. When the record doesn't include the information designated as mandatory then the record may not even be scored and returned as a match to a search query. For example, if the exact last name was mandatory, then only records which included an exact match to the last name would be scored and returned as part of a search query.

In the scoring example above, different possible value perturbations in a field are introduced and scored. For example, one or more digit mismatches (one or more mismatches of a number, character, symbol, etc.) can be matched and scored. As another example, all or a portion of a field can be matched and scored, such as an entire social security number can be matched or a portion of a social security number can be matched. In yet another example, phonetic spellings or synonyms of terms can be matched and scored (e.g., mail and male for sex or John and Jon for a first name), such as but not limited to phonetic spellings of a name. In another example, a single character match of a first letter of a name is scored. In yet another example, match to a name off by only a single character can be scored.

Further, some of the fields can be multivalued. Thus, the score from a query of particular field can result in multiple matches within a single healthcare record where each match contributes to a score. For example, an amount can be contributed for each match to a phone number in the phone field, such as a first amount for one match, a second amount for two matches, a third amount for three matches, etc. In addition, data can be designated as current or valid, such as a current address or a current phone number. In one embodiment, a score amount can be designated for a match to a current address or a match to a previous address where the score amounts can be the same or different depending on whether the match is to a current address or previous address.

In one embodiment, the last name can be multi-valued. For instance, a person can change their name as a result of some event, such as a marriage or an adoption. The system can be configured to search over all of the last names in the inverted index of the MPI database. In this example, a match to the most recent last name is given a higher score than a match to a previously entered last name. Thus, two scores are shown for the lastNameExact, lastNamePhonetic and lastNameSingleCharacter of [1500, 900], [700,500] and [1400,900].

This type of scoring can be implemented in any multi-value field where some indicator is provided which distinguishes between values in the field. For example, information can be considered current or historical, such as a current address, where the current information can be given more weight than the historical information. In another example, information can be considered active or valid versus inactive or expired. For example, information associated a valid driver's license in the personal ID field can be given more weight than an expired driver's license stored in the personal ID field.

In yet another example, multiple values in a field can be identified according to a type or some other delimiter. The type can be used to provide more duplicate scoring options. For example, personal ID types can include a library card, a driver's license, a passport, a green card, a social security card, a voter registration card, a birth certificate, a student ID, etc. Different scores can be assigned to matching scores to different types of information in the same multi-valued field. For example, a match to information from a valid state issued driver's license can be given higher weight than a match to information on a library card.

In the instances where different searching algorithms are applied to a field in a healthcare record, the searches on a particular order can be performed in some order and only proceed to the next search type if the first search is unsuccessful. As an example, for searches involving the last name, the system can first attempt to an exact match in a healthcare record. When the exact name search is successful, the score associated with the exact match is determined and added to a cumulative score. When the exact name search is not successful, the next type of search is implemented. In this example, a phonetic search can be carried out. Again, if the phonetic search is successful, the score associated with the phonetic match is added to the cumulative duplicate probability score.

When the phonetic search is unsuccessful, the system can attempt a search where an attempt is made to match some portion of the last name, such as a one or more of the first characters of the name or a match off by one or more characters. If a match is successful for these searches, than the amount to contribute to cumulative score is determined. If none of the different types of searches are successful, than the field may not contribute to the duplicate probability score. If one more of the searches are mandatory and none of the mandatory searches were successful, than the system may not score the record even if other fields were matched.

In another embodiment, each of the multiple searches can be applied to a field over the entire MPI database and matches for each type of search can be determined. In the instances, where a single healthcare record, matches multiple searches to a particular field, the system can be configured to limit a contribution to a duplicate probability score to only one of the matches. For example, a healthcare record which is an exact match to a healthcare record is also a match to a last four digits of a social security number. However, only one of the matches may be allowed to contributed to a duplicate probability score.

In alternate embodiments, the system can be configured to carry out two or more different search types on a field in the healthcare records where matches to all the searches can contribute to a duplicate probability score. For example, the system can perform a first search type on a field. When a successful match occurs, a contribution to the score can be determined. Then, independent of whether the first search type on a field is successful, the system can perform a second search type on the field. When the second search type is successful, i.e., a match is found, the system can determine a value to contribute to a probability score from the match to the field. Thus, two or more different types of searches can be performed on the same field where a match from each search type can contribute to a duplicate probability score. Typically, the two searches which are allowed to contribute to a score in this manner will be mutually exclusive of one another, i.e., match from a first search type on the field may not be automatically a match to a second search type on the field.

In some instances, a source of data can be identified in the healthcare records in the MPI database. For example, one of the facility IDs can be used to identify the source of the data. In one embodiment, the scoring can be affected based upon the source of the data. For instance, matches to data from a first source can be given a greater weight than matches to data from a second source because the first source is generally considered to be more reliable than the second source.

In another embodiment, the scoring weight can be also given to a selected field if the field is known to be more precise when coming from a particular source. For example, in a first source of healthcare records, the last name field may be known to be more precise than last name field from one or more other sources of healthcare records. Thus, a last name from the first source may be given more weight than from the other sources. However, the remaining data in the other fields of the healthcare records from the first source may not be deemed any different from other sources of healthcare records. Thus, the remaining data in the other fields may not be weighted differently.

In general, scoring weight can be done on a field by field basis where the fields may be each weighted differently even within health records from the same source. For example, a first field of a health record from a first source while may be determined as more precise and given a first scoring weight. Whereas, a second field of a healthcare record from the first source may be determined as less precise and given a different second scoring weight.

Returning to FIG. 3, each time a search and scoring is a carried out, it can be implemented over the entire healthcare information database 54, i.e., a search of all records, in the database 54. In traditional methods, a blocking search is used where first some information in the search is used to limit the portion of the database which is searched. For example, if a search was implemented, on a last name starting with the letter "s," than a search for duplicates might be carried out only on the names starting with the letter "s." Then, once the search is limited (blocked), a table of links is consulted where the table of links includes information indicating the relationship between the limited set of records in the blocked search, such as whether they are possibly duplicates or not.

In a traditional MPI, the table of links is constructed when the database is first formulated. The table of links is formulated based upon a specified algorithm. The building of the table of links can take a very long time, where the amount of time increases as the number of healthcare records in the database increases. Thus, once the table of links is built, it is usually updated very infrequently or even may never be updated in a traditional MPI database.

In traditional systems, the specified algorithm used to build the table of links is usually tested with some initial set of data. However, once the table of links is built, it is not possible to improve on the algorithm or customize it to particular set of data, such as portion of the MPI database which is subsequently added. When the algorithm used to construct the table of links is changed, the relationships in the table of links are no longer valid. In embodiments described herein, a table of links is not constructed. Further, each time a duplicate search is requested, it can be performed on the entire MPI database. Since the links are not saved, a new duplicate detection algorithm can be introduced on the fly. For example, duplicate probability scoring algorithms can vary from search to search and may even be user customizable, i.e., the system may allow a user to specify parameters which alter the search algorithm. As another example, duplicate probability scoring algorithms can be customized to healthcare record data sets associated with a particular organization.

In FIG. 3, a first organization 102 and a second organization 104 are shown. In organization 102, two users, 122 and 124 are shown performing operations involving generating duplicate probability scores and accessing the healthcare information 54 via interfaces 118 and 120. In the second organization, a single user 130 is shown performing duplicate scoring operations via interface 128. The number of users and interfaces which are generated over time can vary and the example in FIG. 3 is shown for the purposes of illustration only.

The first organization 102 and the second organization 104 can each have their own duplicate probability scoring algorithms, 110 and 112, respectively. A healthcare information database, such as 54, can include millions of records and can be accessed by more than two organizations. It is possible that tens, hundreds or thousands of different organizations may access a healthcare records database where each organization can have their own custom duplicate probability scoring algorithms, such as 110 and 112. The users can be using the system simultaneously. Thus, the system can be simultaneously generating duplicate probability scores using a number of different scoring algorithms which are organization specific. The combination of scoring algorithms which are applied at a particular time can depend on the combination of users from different organizations with different scoring algorithms which are accessing the system at a particular time.

In FIG. 3, organizations 102 and 104 may have access to some subset of the healthcare information database. For example, organization 102 may be able to see records associated with a first set of patients and organization 104 may be able to see records associated on a second set of patients where there may or may not be overlap between the records which each organization can view. Thus, even when a search is carried out over the entire database, the system can be configured to only return the matches from within among the patients each organization is allowed to see.

As an example, the system may identify three duplicate matches from a search within the database 54. However, organization 102 may be only allowed access to two of the matches and hence the system may output only the two matches. A system operator performing the same search and may not have such limitations. Thus, all three matches can be output to the system operator.

In the healthcare information database 54, a first subset of patient data 106 is shown accessible to organization 102 and a second subset of patient data 108 is shown accessible to organization 104. In each of these datasets, 106 and 108, there can be an issue with the reliability of the data sets, such as a common typographical error, which can be accounted for via the querying and/or scoring functions to provide better duplicate matching. The issue with each of the data sets and a duplicate probability scoring solution can be set dependent. Since only one organization accesses either of the datasets, it may not make sense to generate a global solution instead, as shown in FIG. 3, a custom scoring, such as 110 or 112, can be used for each organization.

In a healthcare organization, different data sets can be added over time. For example, one healthcare organization can merge with another healthcare organization. As the new data is added, the scoring algorithm which was appropriate for the database at a first time may not be as suitable when the new data is added. With embodiments described herein, since links between records are not saved, a new algorithm can be developed and easily applied. However, with traditional methods, the application of new algorithm is difficult because a new table of links between the records needs to be built which takes months for a large database. Thus, when new data is added to a database using traditional duplicate scoring techniques, it is unlikely that a new duplicate scoring formulation is going to be applied. Instead, the old duplicate scoring algorithm is going to be applied to the newly added data.

In FIG. 3, a first search query is implemented via interface 118. For this query, none of the information in data 106 is accessed. Results 114 are returned from the search query. A second scoring query is implemented from interface 120. In this example, results are returned from inside data 106 and outside data 106. Different duplicate probability scoring can be used for records from healthcare records within data 106 as compared to records outside of data 106. The duplicate probability scoring results 116 for this query are shown with a component A and a component B to illustrate the different duplicate scoring formulations used for the records within and outside of data 106.

Although the different duplicate scoring formulations can be applied to first healthcare record as compared to a second healthcare record, the healthcare records can be still compared on a common scale. For example, a common threshold value can be selected for both scoring duplicate scoring formulations for indicating a duplicate match. When the common threshold is exceeded, healthcare records scored using either formulation can be designated a duplicate match and the scores for both records can be output with the designation.

In another embodiment, the thresholds can be different for the two different duplicate scoring formulations, i.e., a first threshold value can be associated with a first duplicate scoring formulation and a second threshold value can be associated with a second duplicate scoring formulation to indicate a duplicate match. In this example, when two healthcare records are duplicate matches where each was scored using different duplicate scoring formulations, the outcome that both records are duplicate matches may be output. However, the scores for each healthcare record may not be output because different scales are used and hence, a comparison of the scores may not be appropriate.

As an example, data 106 can be designated as extremely reliable and records in this data set might be given a higher score as compared to other records not in the data set. In another example, one field from healthcare records in data 106 can be considered very reliable while another field might be considered unreliable. Thus, matches to the reliable field in data 106 can be given a higher contribution to a duplicate probability score as compared to matches in this field outside of data 106. Whereas, matches to the unreliable field in data 106 may be given a lower contribution to a duplicate probability score (i.e., lesser weight) as compared to matches to the field outside of data 106.

A similar example is shown for organization 104. In 112, search query matches to healthcare records in data 108 can be scored different than matches to data outside of data 108. The results 126 of a query involving results from inside and outside of data 108 are shown. A first component of the results, component A comes from scored matches from healthcare records in data 108 whereas a second component of the results, component B, comes from scored matches from healthcare records outside of data 108.

Next a few methods of utilizing an MPI system providing duplicate scoring are described. FIG. 4 is a flow chart of a method 200 of managing an MPI system including an MPI database with inverted indices and probabilistic duplicate scoring. In 202, healthcare records from a plurality of different sources, such as different healthcare organizations can be received. In 204, the records which may have heterogeneous formats can be converted to a homogenous format associated with the MPI database.

The record format for the MPI database can include a number of different fields. In 206, string values, which can include numbers, letters, symbols, control characters, etc., can be determined for each field. In one embodiment, the string values can be generated by surveying the contents of each field of all the healthcare records and identifying unique strings. In 208, using the determined string values, an inverted index can be constructed for each field over the entire database. The inverted index includes pointers for each string value which points to the one or more healthcare records in which the string value appears. In duplicate probability scoring, when a field is searched as a result of a search query, the inverted index covering the entire database can be searched according to the input associated with the field which is received in the search query. Matches to a search query within the field can contribute some amount to a duplicate probability score. The search query can involve a search over a number of different fields. Thus, the duplicate probability score for an individual healthcare record can include contributions from a number of different fields within the healthcare record.

In 210, scoring parameters can be received. The scoring parameters can include weights which are assigned to detected matches in a record. The weights can be used to determine how much a match within a field contributes to a duplicate probability score. For example, in one embodiment, a contribution value can be assigned to each match in a field of a healthcare record where a sum of all of the matches provides a total duplicate probability score for the record. The total duplicate probability score for the healthcare record can be compared to one or more defined threshold values associated with different value ranges. Depending on where the score falls within the ranges, the record can be classified as a likely duplicate record or not. The system can be configured to allow a user to vary these threshold values. In one embodiment, a probability of a record being a duplicate can be determined and probability ranges between zero and one can be defined which indicate whether a record is likely a duplicate or not.

In 212, search inputs can be received, such as via an interface associated with the MPI system. Based upon the search inputs, a search query can be constructed. For example, a first name and a last name can be received and a search query for searching the inverted indices for the first name and the last name can be constructed. In 214, the inverted indices of the master database can be searched to identify records with one or more fields which match the query parameters. In some instances, certain information may have to be matched, i.e., the information may be designated as mandatory for the record to be returned as a search result.

In 216, the scoring parameters used to indicate a likelihood of a record being a duplicate can be determined. For example, as described above, an organization can use custom scoring algorithms. Thus, in 216, the system may receive information that identifies an organization and then retrieve the scoring parameters for the identified organization. In another embodiment, custom scoring may be associated with certain portions of the records. Thus, depending on identification information associated with a record with a match to a query, different scoring parameters can be applied. Thus, after identifying a match in a record, the system may retrieve scoring parameters which are used to determine the duplicate probability score for the record.

In 218, based upon the determined scoring parameters and type of match, i.e., which field the match occurred, a duplicate probability score which reflects the likelihood that a healthcare record is a duplicate record can be generated. In 220, the healthcare records can be sorted and categorized according to the generated scores. In one embodiment, a record in a set of retrieved records can be designated as the master record. The master record can have the highest score and can be output first via the interface. In addition, as will be described below with respect to FIG. 7, the MPI system interface can provide tools for comparing information in the master record to other records which have been identified in the query.

When two records have the same score, the record which is most completely populated can be output as the master record. In a query, some portion of the fields of a record can be searched. Based upon the fields which are searched, two records can have the same score. However, one record when all of the fields are examined include fields not search in the query may be more complete than the other record. Thus, for a tie score, the record which is most complete can be identified as the master record. In one embodiment, for a tie score, the entire duplicate scoring formulation, i.e., the contributions from all the fields which are given a contribution value, can be applied for each healthcare record to determine which record is the master record.

In 222, based upon the sort according to the score, the categorization of records according to their score (e.g., a record can be scored as a match or a probable match) and the access privileges of a user, a master record and other linked records according to the scoring algorithm can be output via a system interface. In a traditional system, a table of links is maintained which indicates the relationship of records in accordance with an applied duplicate record scoring algorithm. In the methods described herein, a table of links is not maintained. Thus, in 224, after a user is finished viewing the records associated with the search query, the links associated with the duplicate scoring for the search query are deleted. For example, a user may implement a first search which identifies a first number of related records and then the user may implement a second search which identifies a second number of related records. When the second search is implemented, the MPI system may delete the information which identified the first number of records as being related and then subsequent delete the information indicating the relationships determined in the second search.

Figure 5:
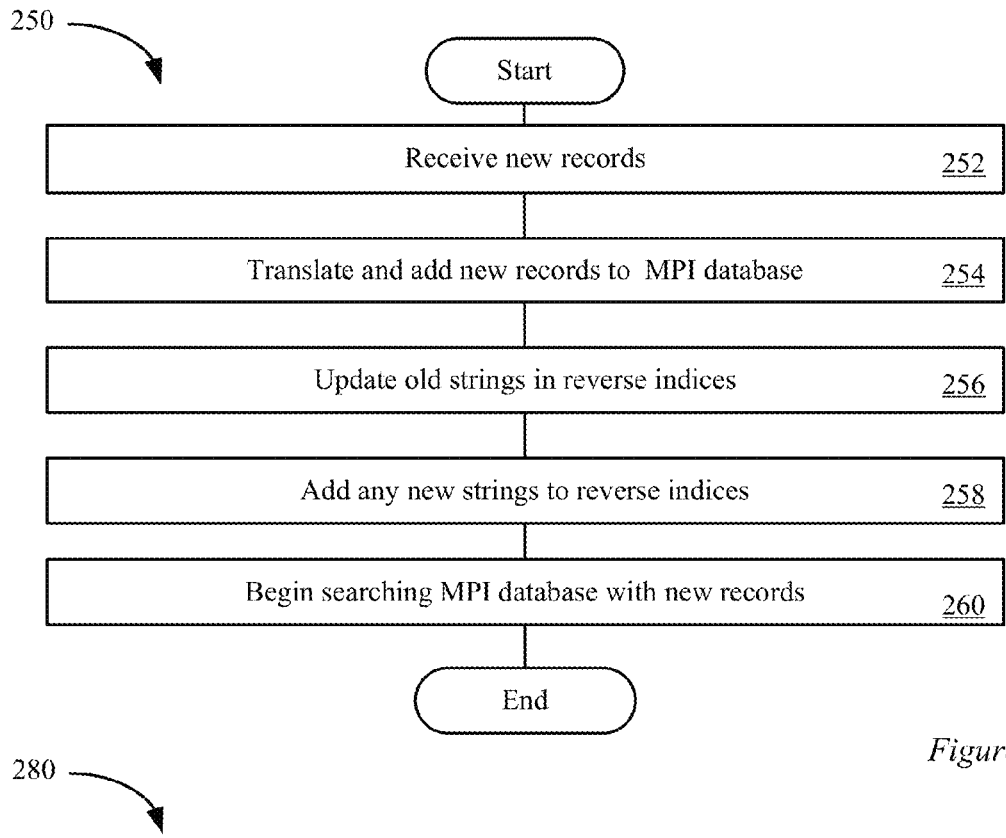
FIG. 5 is a flow chart of a method of updating an MPI database using inverted indices in accordance with the described embodiments.

FIG. 5 is a flow chart of a method 250 of updating an MPI database using inverted indices. In 252, one or more new records can be received. As an example, a new record can be received when a new patient is registered in an organization. As another example, new records can be added to the database when two healthcare organizations merge.

In 254, the received records can be translated and added to the MPI database. The translation may involve mapping the information in the received records to the format associated with the MPI database. In 256, the existing string values in the inverted indices can be updated. This step may involve determining whether the existing strings appear in any of the fields of the newly added records. When an existing string value appears in one of the newly added records, then a pointer can be added which points to the record in the MPI database containing the existing string value.

The inverted index involves mapping occurrences of values which appear in a field of data to a location. In one embodiment, the location can be in a particular healthcare record. In another example, the location could be in a file or a document of some type where the value is stored. A pointer can provide the information that links one instance of an occurrence of a particular value in the field of data to a respective location where it is stored. Each unique value in a field of data can occur in one or more locations, such as a common last name appearing in multiple healthcare records. Thus, a given unique value in a field of data, which is indexed, can be associated with multiple pointers where each pointer points to a location where an occurrence of the unique value can be found.

When new records are received, each value appearing in a data field of the new records, which is to be indexed, can be compared to existing values stored in an inverted index. When a particular value in a record is determined to be the same as an existing value, then a new pointer can be added in the inverted index which is associated with the existing value and points to the location where this new occurrence can be found. If a value in a data field of the new records doesn't match any of the existing values in the inverted index (e.g., a last name which is different from any last name stored in the index), then the new value can be added to the inverted index and a pointer can be associated the value where the pointer indicates the location where the value occurs.

As an example, if the inverted index for last name includes the name "Smith" and a new record is added with the last name smith, then the inverted index can be updated such that the string for "Smith" in the inverted index points to the unique identifier in the MPI database for the new record. Each new record can be assigned a unique identifier associated only with the MPI database. Thus, the pointer for the string "Smith" can point to the unique identifier for the newly added record including the last name "Smith."

In 258, new string values can be added to the inverted indices. For example, if the new records include the last name "Smith" and the last name "Smith" hasn't appeared before in the MPI database. Then, the string value "Smith" can be added to the inverted index for the last name along with a pointer to the newly added record including the last name "Smith." Subsequent searches of the inverted indices which match the string "Smith" in some manner will then identify the healthcare record including the last name "Smith."

In 260, new searches and duplicate scoring can be generated using the updated inverted indices. In one embodiment, a new scoring algorithm different from the one used prior to adding the new records can be utilized. For example, a scoring algorithm, which is specific to only the new records which were added, can be used.

Figure 6:
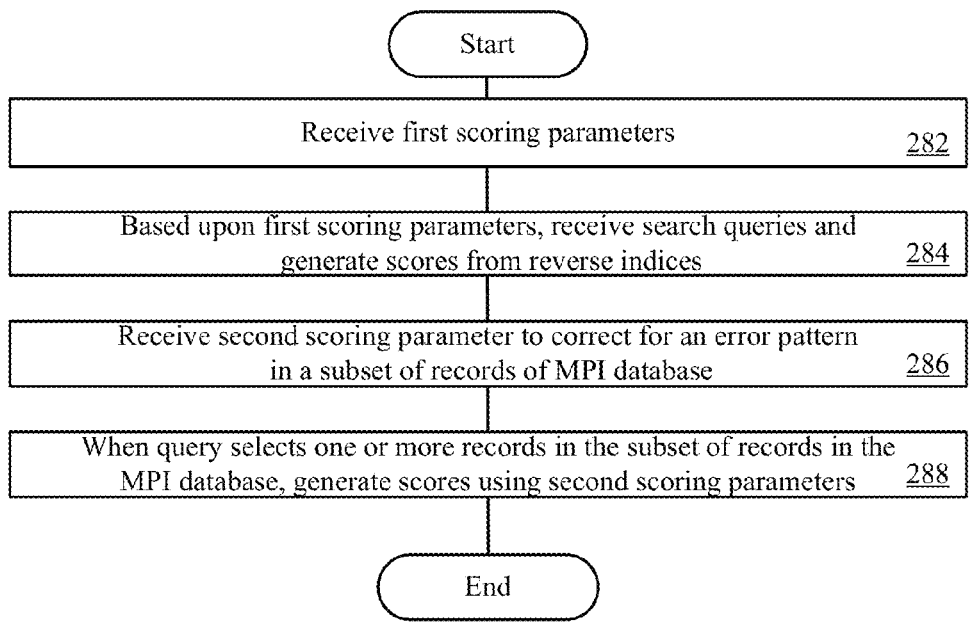
FIG. 6 is a flow chart of a method of adjusting duplicate scoring in an MPI system having an MPI database using inverted indices in accordance with the described embodiments.

FIG. 6 is a flow chart of a method 280 of adjusting duplicate scoring in an MPI system having an MPI database using inverted indices. In 282, first scoring parameters which are used to weight information associated with a duplicate scoring algorithm can be received. In 284, based upon the first scoring parameters, receive search queries and generate scores using the inverted indices associated with the MPI database. Next, a data pattern in a subset of the records can be identified. The data pattern can pertain to one or more fields in all or a portion of the records. In one embodiment, the data pattern can be a pervasive error in data entry, such as not completing or incorrectly completing a particular field in one or more records in a particular way.

In 286, a second set of duplicate scoring parameters can be received to correct for the data pattern in the subset of records. The query structure can also be altered to identify and match the data pattern. The duplicate scoring parameters can improve the capability of the system to better identify duplicate records. The new duplicate scoring parameters may apply to only portion of the records in the MPI database and within those records only certain fields. In one embodiment, the new duplicate scoring parameters may be organization specific in that only a particular organization may have access to the portion of the records in the MPI database for which the new scoring parameters were developed. Thus, the new scoring parameters may only be applied when the system determines someone from the particular organization is performing a query.

In 288, when a query matches one or more records in the MPI database to which the new scoring parameters apply, the duplicate scores for these records may be generated using the new scoring parameters. In one embodiment, the new scoring parameters can be applied to all of the records in the MPI database. In another embodiment, old scoring parameters can be used for a first portion of records in the MPI database while the new scoring parameters may be applied to a second portion of the records in the MPI database. In general, a plurality of scoring algorithms can be developed which are applied to different portions of the MPI database.

MPI System User Interface Features

Figure 7:
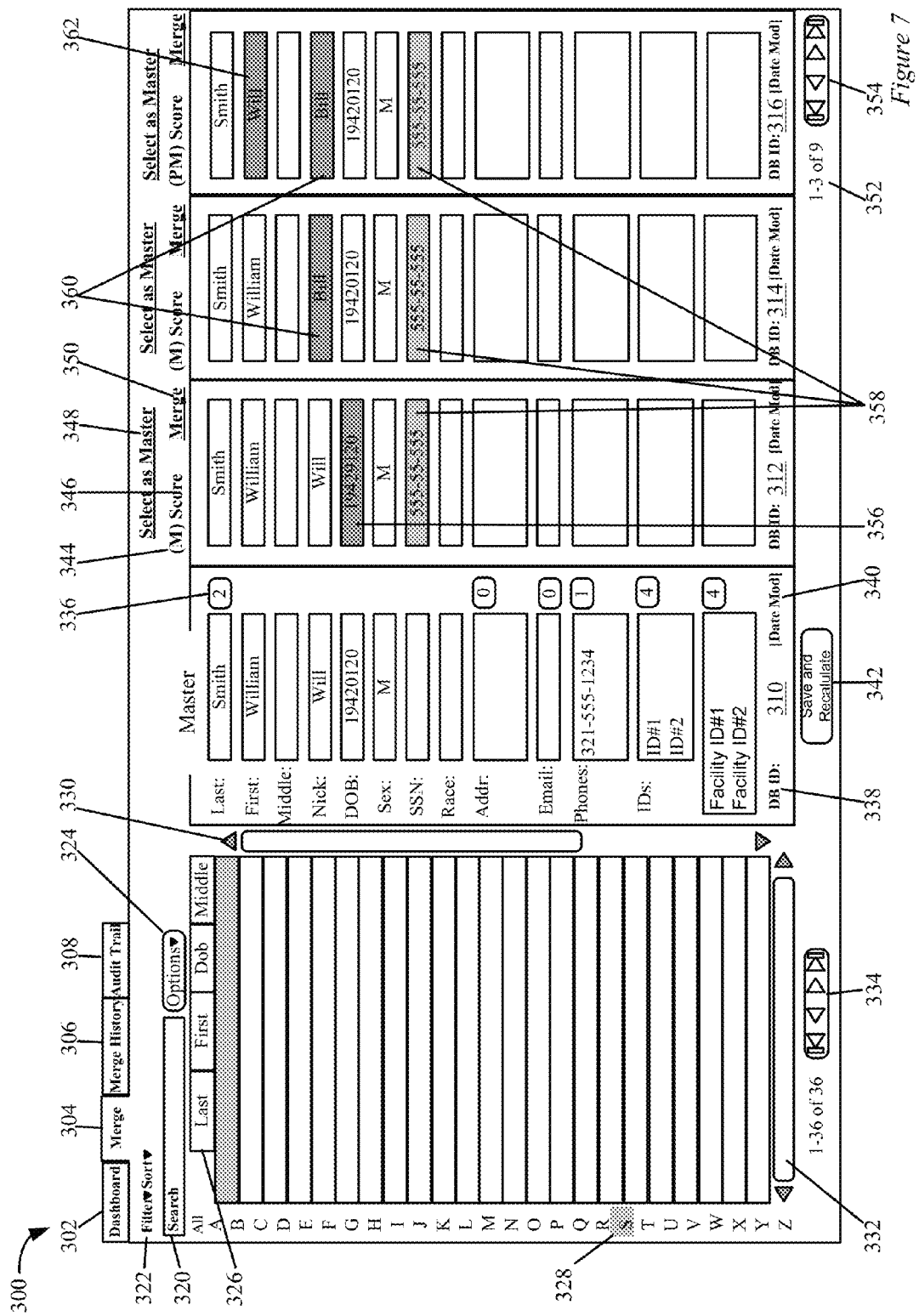
FIG. 7 is an illustration of a state of a MPI system interface including data comparisons of duplicate records in accordance with the described embodiments.

Next, details of an MPI system interface are described with respect to FIGS. 7-12. The MPI system interface allows users to access various functions of the MPI system. FIG. 7 is an illustration of a state of a MPI system interface 300 including data comparisons of records returned from a search query. In one embodiment, the functions of the MPI system interface can be grouped into four categories: 1) dashboard 302, 2) merge 304, 3) merge history 306 and 4) audit trail 308. Access to interface states associated with each of these groups of functions can be accessed via tabs in the interface, such as 302, 304, 306 and 308. Different groupings of features can be used in an interface, which include more or less categories with different functions assigned to each grouping. Thus, the groupings associated with each tab are providing for the purposes of illustration only and are not meant to be limiting.

Figure 9:
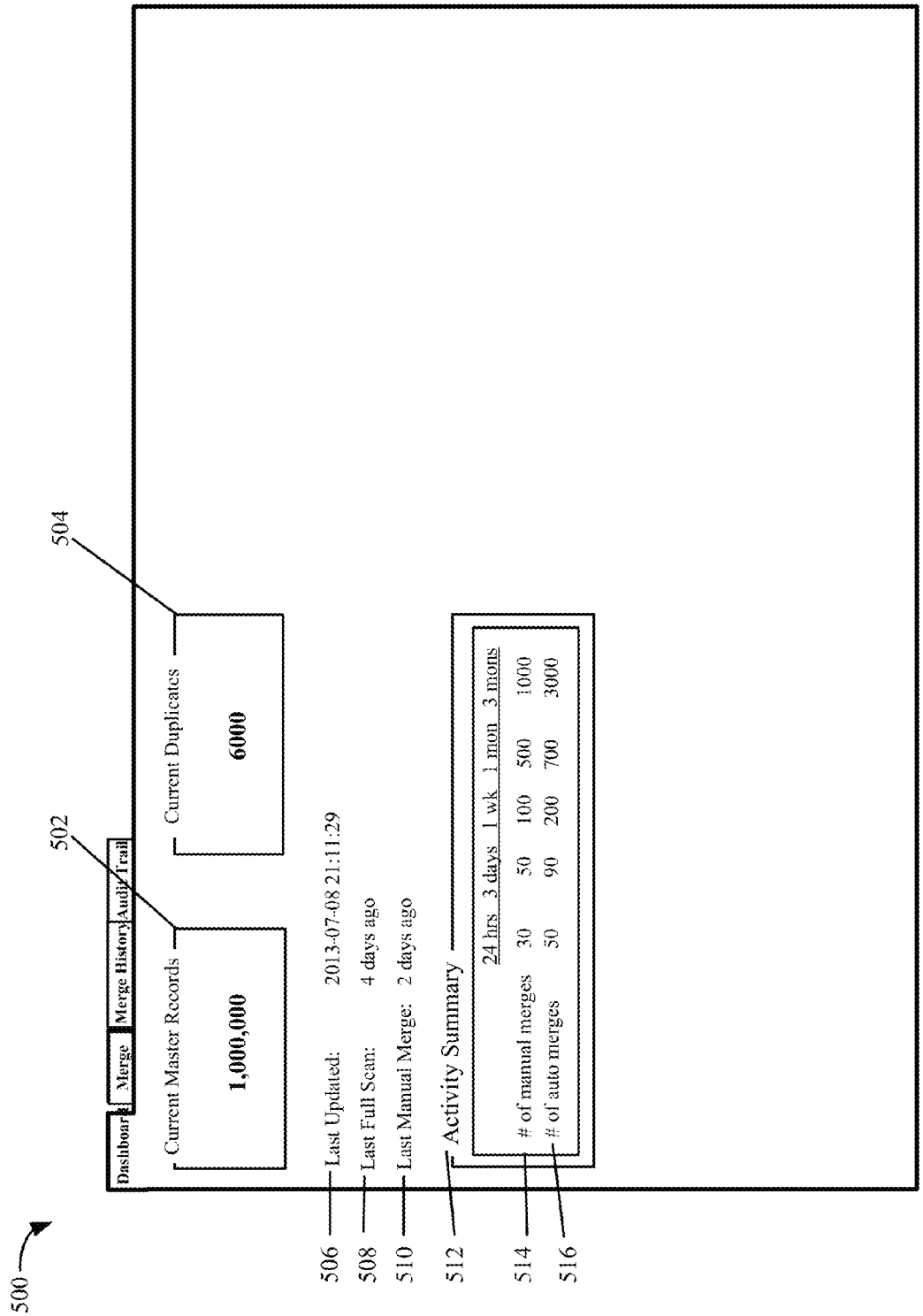
FIG. 9 is an illustration of a state of a MPI system interface showing a user dashboard in accordance with the described embodiments.

The dashboard 302, which is described in more detail with respect to FIG. 9, can show information about an organization's records in the MPI database including a number of identified duplicates and efforts to reduce duplicates. The merge 304 functions allow records identified as possible duplicates to be compared to one another and modified.

The merge history 306 allows a user to view modifications to a healthcare record over time and possible inverted changes. For example, two merged records can be separated or a previous state of a record in the past can be viewed. The merge history 306 is described in more detail with respect to FIG. 10. The audit trail 308 can show information about how the MPI database is being accessed and what actions are being performed by users. An audit trail interface state is described in more detail with respect to FIG. 11.

A search box 320 can be provided. The search box 320 can configured to receive free text input used in a search query. As described above, the search input can be used to form a query of the inverted indices over the entire MPI database. The filter/sort 322 buttons can be selected to provide options for filtering and sorting results returned from a search. A selection of the options button 324 can cause different search query options to be displayed. For example, via the options button, it may be possible to turn on or off different search query options, such as performing only a search form an exact match to a last name as opposed to an exact match, a partial match and a phonetic match.

Below the search options, a directory of records in the MPI database presented in alphabetical order is shown. A selection of a letter, such as the "R" 328 can cause last names starting with the letter "R" to be displayed. Information associated with each record, such as last name, first name, date of birth and middle name are displayed. This information is in alphabetical order and can appear in each of the rectangular boxes below the record fields 326. A slider bar 332 is provided. A selection of the slider bar 332 can cause the fields 326 displayed with the records to change. For example, sex, social security number can be displayed for the patients listed on the page.

In one embodiment, it may be possible to sort the records according to different parameters or fields. For example, the records can be sorted in reverse alphabetical order by last name or first name. As another example, the records can be sorted according to date of birth. In general, the records can be sorted according to any of the fields and then output via the system interface.

The slider bar 330 and arrow tool 334 can allow a user to move through the records. For example, selecting the slider bar 330 and changing its position can cause the records displayed to go up or down in alphabetical order. The arrow tool 334 can allow user to advance through the data on a page by page basis and jump to the first page and the last page of records. In this example, thirty six pages of records are shown.

In 300, a number of potential duplicate records are shown which match a particular query which can have been entered via text box 320. As described above, a record with the best match to the query can be designated as a master record. The master record is search dependent and not a property which is stored about the record. Thus, for a first search, a first healthcare record in a first group of healthcare records associated with the search can be designated as the master record. Then, for a second search, a second group of records can be identified as possible duplicates. The first healthcare record can be a member of the second group but another record with a higher score according to the second query can be designated as the master record.

In one embodiment, within a group of records designated as possible duplicates according to a query, the interface can be configured to allow a user to select another record as the master. For example, the user can select link 348 to designate it as the master record. A number of comparison features can be provided which compare the master record to a number of potential duplicates and highlight differences between the duplicate records relative to the designated master record. Thus, by selecting another record as a master, a different comparison among a group of records can be generated.

In 300, a master record 310 and three duplicates, 312, 314 and 316 are shown on the page. As indicated in 352, a total of nine duplicates have been identified and the first three are output. The arrow tool 354 is selectable to cause a different portion of records in the set of nine to be displayed on the page. The number of records which can be displayed on the page and the total duplicates from a search is variable and is not limited to the example in the figure. Thus, in 300, the example is provided for illustrative purposes and is not meant to be limiting.

Figure 10:
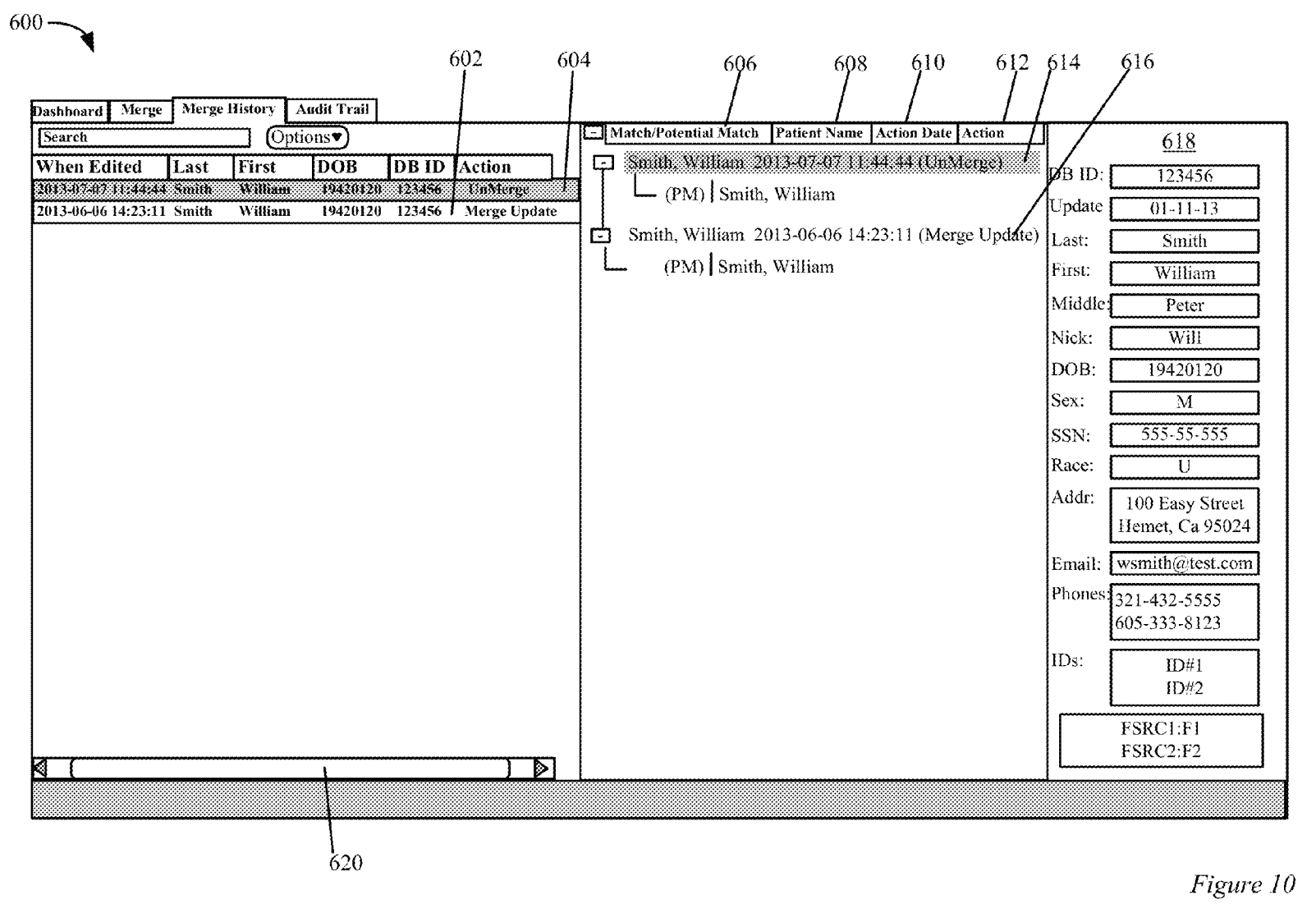

For each record, a number of fields are displayed. These fields were described above with respect to Table 1. In addition, for each of the master record and the duplicates, a unique database ID, such as 338, is listed. The unique database ID may be the identifier to which the string values in the inverted indices point. Further, the last time 340 the record was modified is displayed. In one embodiment, a selection of the date modified can cause a merge history for the selected record to be displayed, such as shown in FIG. 10.

In various embodiments, the interface 300 can include controls which allow additional fields in the records, which are not shown, to be displayed. As mentioned above, many of the fields may be multi-valued. A number, such "two" on a button, such as 336, can appear by all or a portion of the multi-valued fields. The button indicates how many values are stored for the field. A selection of the button can cause additional values for the field to be displayed. For example, when the button 336 is selected, the two last names stored in the field can be output in some manner. For example, the "Smith" and "Smithson" may appear in a pop-up box representing two last names associated with the individual in the master record.

For each of the duplicate records, 312, 314 and 316, a score, such as 346, can be displayed. The score can be duplicate probability score as described above. As previously described, different categories can be defined for a duplicate probability score and given a name. The categories can be defined as a range of score values. In this example, a score above a first threshold value can be referred to as a match, which is indicated by the "M" 344. A probable match (PM), can be assigned to a healthcare record with a score below the first threshold value but greater than a second threshold value. In 300, record 316 is indicated as a probably match.

A comparison feature can be provided which compares the information in the master record to each of the duplicate records on a field by field basis. In one embodiment, the interface can provide a user selectable option which allows this feature to be turned on or off or customized by a user. The comparison feature can graphically highlight differences between each duplicate and the master record. In one embodiment, differences can be graphically highlighted using different colors (e.g., red, green, yellow, etc.), different fonts (e.g. bold font), color patterns (e.g., flashing pattern), to draw a user's attention to the differences between the records in the comparison.

In 300, the master record includes the first name, "William," duplicate records 312 and 314 also include this first name. However, duplicate record 316 includes the name "Will" 362 instead of "William" and this difference is highlighted. If duplicate record 316 is selected as the master record, then, in a comparison of this record to each of records, 310, 312 and 314, the name "William" in the records may be high-lighted. Since in this case, "William" would be different than the name "Will" associated with the master record.

A nickname "Will" is associated with the master record. Duplicates records 314 and 316 designate the nickname "Bill" 360. Thus, the fields containing the nickname "Bill" are high-lighted. When nickname is a multi-valued field, the name "Bill" can be added to the nickname field in master record 310 to account for the additional nickname. After an update of this type, the master record 310 can include a first value of "Will" in the nickname field and a second value of "Bill" in the nickname field.

For record 312, the date of birth 365 is off by a single digit as compared to the master record. Thus, the date of birth 365 is graphically highlighted to indicate the difference between the records. A phone number 358 is provided in each of records 312, 314 and 316. The phone number 358 is highlighted because the master record doesn't have any phone number. The phone number was shown as being the same for the all duplicates. In other scenarios, the phone numbers in records 312, 314 and 316 can be different but can still be high-lighted because the master record doesn't include a phone number. In this example, if one of records 312, 314 or 316 is selected as the master record and compared to the other records including 310, then only the phone number field in 310 would be highlighted because records 312, 314 and 316 each share the same phone number.

When a user wishes to modify information in one the records, such as master record 310, a user can select one of the high-lighted fields. In some embodiments, it may be possible to drag and drop information from a duplicate to the master or from a master to the duplicate and then select the "save and recalculate" button 342 to finalize the transaction. In addition, a selection of the merge link 350 can cause a merge between two records to be initiated. In yet another embodiment, a selection of one of the fields, such as a multi-value field, can cause the interface to generate a state which causes details about the multiple values in the field to be displayed and exchanged between a master record and a duplicate record, which is described in more detail as follows with respect to FIG. 8.

Figure 8:
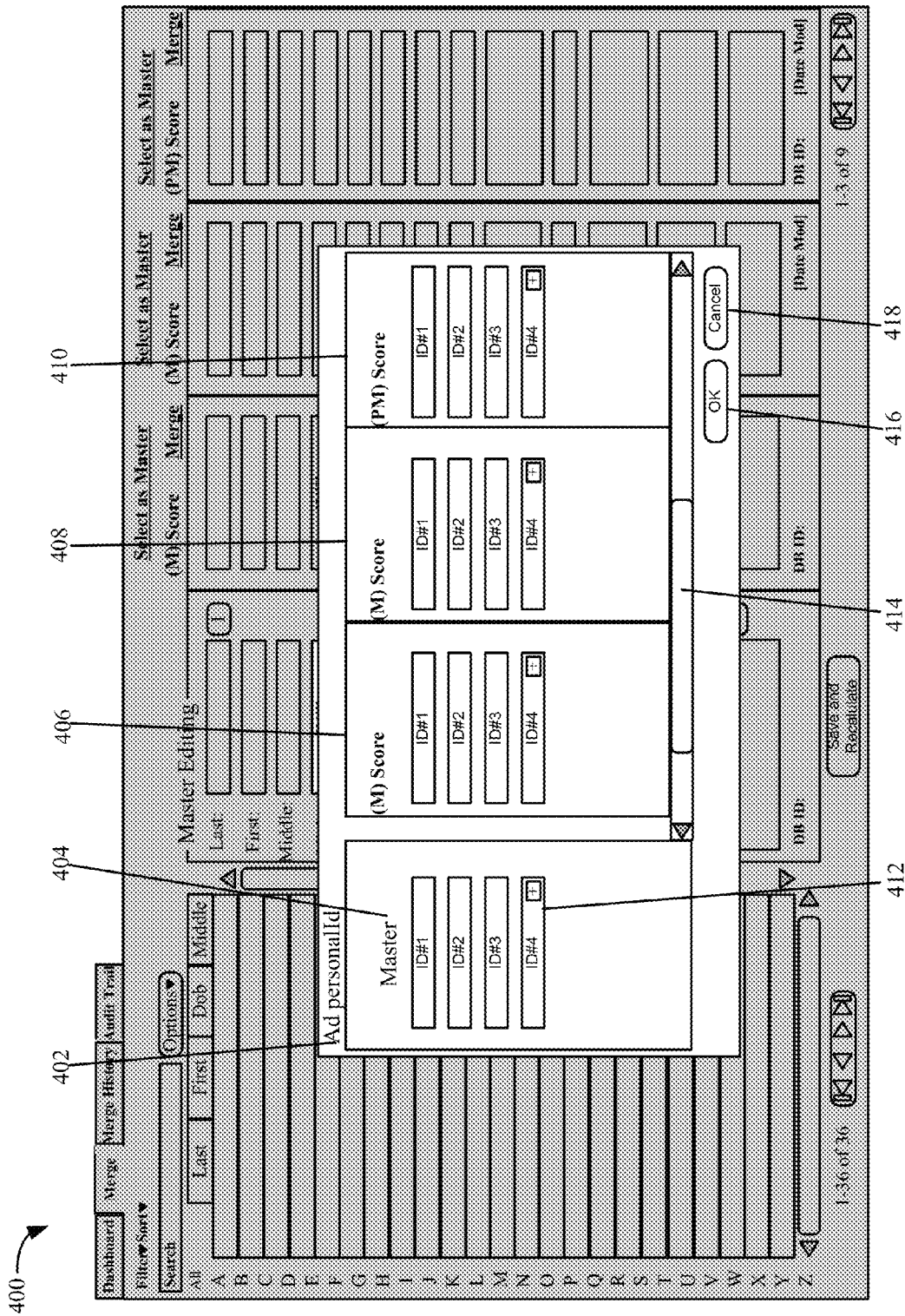
FIG. 8 is an illustration of a state of a MPI system interface in a state allowing modification of a data field in accordance with the described embodiments.

FIG. 8 is an illustration of a state of a MPI system interface 400 in a state allowing modification of a data field in accordance 402. In the example, the personal ID data field 402 is selected and a pop-up window is generated which shows a master record personal ID field 404 and the personal ID fields, 406, 408 and 410. Within the records, fields can be examined such as 412. If there are more duplicate records than the pop-up window allows to be seen, then the slider bar 414 can be selected to allow additional duplicate records to be made available on the pop-up window. In this example, the duplicate records are listed in according to their duplicate probability score from highest to lowest.

Although not shown, differences between the master record and the duplicate records can be high-lighted. The various values of the field can be expanded to show details of each field. In one embodiment, a master record can be updated by dragging information from fields in the duplicates to the master record. For example, the master record and the duplicate record may include a description of a common ID, such as a driver license. However, the duplicate may be deemed more complete. Thus, the more complete information can be dragged from the duplicate to master so that the master's field is more complete. In some instances, the duplicates (in general, any of the records returned from the search) can include descriptions of an ID not found in the designated master record. Using the interface 400, it may be possible to add a new value to the personal ID field in the master record and then copy information associated with the ID from one of the duplicate records to the new value in the master record.

When a user is finished with the modifications to the master record, the "ok" button 416 can be selected. Then, the changes can be saved and the interface can return to state 300 shown in FIG. 7. Further, audit information and merge history information can be saved. If the user decides not to make any changes, the cancel button 418 can be selected the interface can again return to the state from which the pop-up was generated, which is state 300 in this example.

Next, the system interface in a state 500 showing a dashboard is described. FIG. 9 is an illustration of a state 500 of a MPI system interface showing a user dashboard. In one embodiment, this state is generated when a tab linking to the dashboard is selected. The interface can display a total number of master records 502. In this example, one million records are displayed. If the interface is generated for an organization, then the number of records may be the number of records associated with the organization. If the interface is being generated for a system operator, then the number of master records can be all of the records in the MPI database.

In particular embodiments, the MPI system can include tools for automatically identifying duplicate records. Further, the MPI system may allow a user to indicate that two or more records may be duplicates and set a flag that indicates the two or more records are to be reviewed. In this example, a current number of duplicates in the database 504 are indicated as six thousand. This value can change over time as new records are added to the database.

The dashboard also includes: 1) the last time 506 the MPI database was updated, 2) the last time 508 the MPI database was scanned for duplicates and 3) the last time a manual merge of two records was performed. In addition, an activity summary 512 is generated. The activity summary 512 indicates the number of manual record merges 514 and automatic record merges performed over different time periods. In one embodiment, the MPI system can be configured to automatically merge records. For example, duplicate records can be merged automatically when the duplicate probability score exceeds a threshold value.

In various embodiments, the activity summary can be broken out on a per person basis, i.e., manual merges performed by various individuals over different time periods. In other embodiments, the duplicates can be output according to some characteristic, such as by individuals or by practice group, or some other common feature which allows potential sources of the duplicate records to be identified. In yet another embodiment, a scheduling tool can be provided. The scheduling tool may allow person to assign some amount of duplicate records for review and keep track of the assigned person's progress, i.e., how many of the assigned records have been reviewed. In one embodiment, the system can include a duplicate record prioritizer which prioritizes the duplicate records in regards to which need to be reviewed first.

Next details of a merge history interface state are described. FIG. 10 is an illustration of a state 600 of a MPI system interface showing merge history information. The merge history page can include information about one or more records, such as 602 and 604. A user may attempt to locate and examine particular records. Thus, the particular records which appear on this page may depend on a particular search criterion. For example, a user may request the system to locate records edited between a particular time period or the user may locate a record by its unique database identifier.

The search box may allow the user to search for particular records to examine. In this example, two actions performed on the same record at different times are listed. At a first time, a merge update was performed on the record, which changed contents of the record. At a second time, an unmerge operation was performed. The unmerge operation can restore a record to a state prior to an action being performed on the record. For example, if information was added to the record, then the unmerge operation can restore the record to its state prior to the information being added. Thus, if two records are merged which should be merged, such as two records identified as duplicates which are not actually duplicates, then the changes can be reversed.

In 600, two records are shown, 602 and 604. A little information about each record is displayed to the interface, such as "When edited," "Last Name," "First Name," "Date of Birth," "Unique database identifier," and action performed on the record. A selection of slider 620 can cause additional about the records to be displayed. The record 604 is selected and more complete information about record is shown in 618.

In one embodiment, a tree structure can be generated which shows a history of modifications to a record. The tree structure can reflect changes to a record over time and any source records for the changes. For example, if two records are merged into a single record, then the tree structure can include information about the two original records and the actions that were performed involving the records. In one embodiment, locations on the tree can be selected and a state of a record in the past can be constructed and output. In example of state 600, information about records in a tree include whether the record was a match or a potential match 606, a patient name associated with the record 608, a date 610 an action was performed on a record and the action 612 which was performed.

Figure 11:
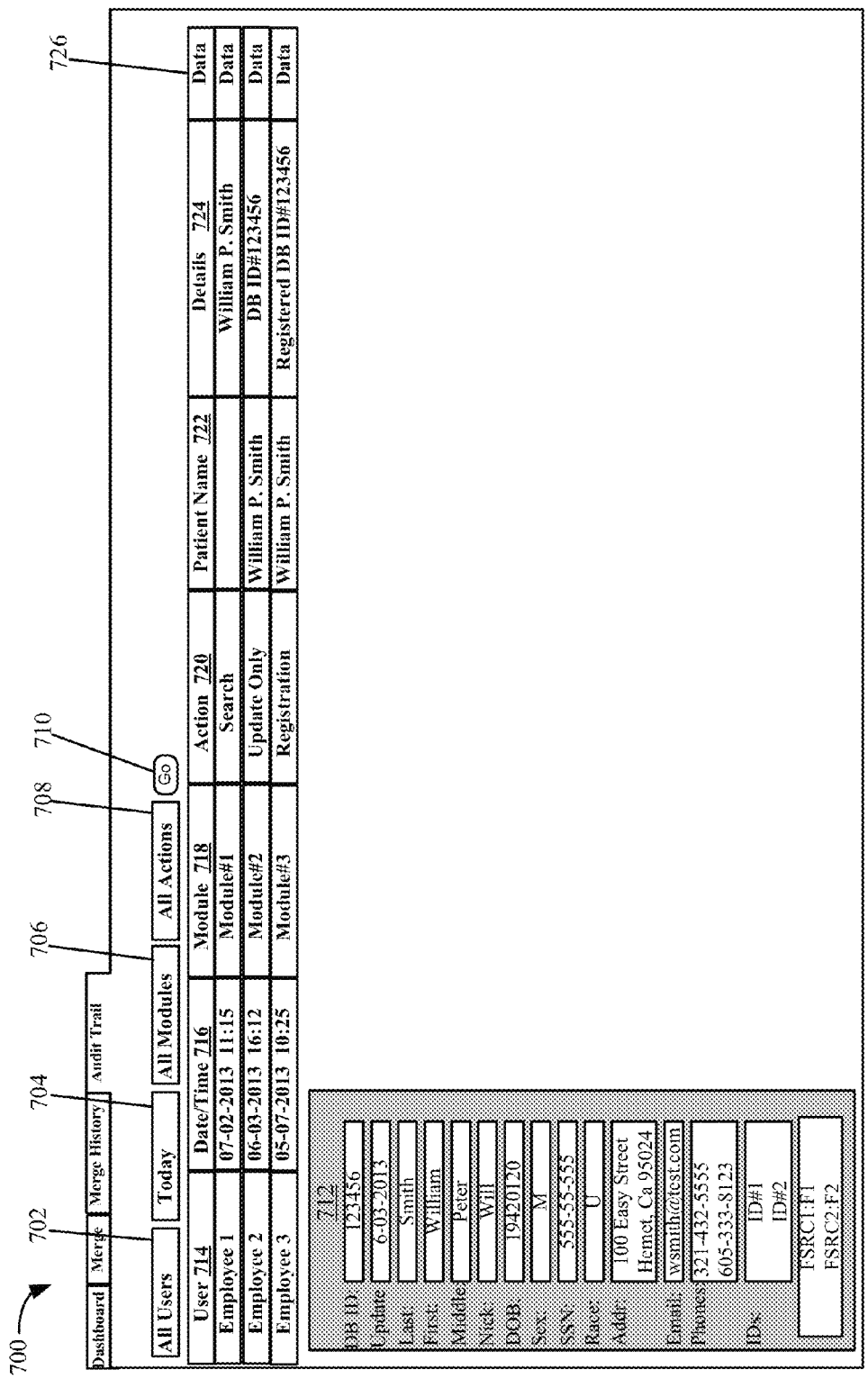
FIG. 11 is an illustration of a state of a MPI system interface showing audit trail information in accordance with the described embodiments.

Next, a state of the interface providing audit trail functions is described. FIG. 11 is an illustration of a state 700 of a MPI system interface showing audit trail information. In one embodiment, the interface 700 may allow user to filter actions performed using the MPI database. As an example, a filter 702 can be provided which allows all or a subset of users to be selected. As another example, a filter 704 can be provided which allows a time period to be selected. In yet another example, a filter 706 can be provided which allows actions associated with a particular software application (module) to be selected. In a further example, a filter 708 can be provided which allows a user to select from one or more types of actions performed, such as an update or a merge. The filters can be selected alone or in combination with one another and then a search can be initiated when the go button 710 is selected.

An example of information returned in a search according to selected filters is provided. The information includes a) a user 714, which is associated with an action on the MPI database, b) a date/time 716 recorded for the action, c) a module 718 which was used to perform the action, d) the action performed 720, e) a patient name associated with the action 722 (if there is only one, such as for a record modification), f) additional details about the action 724 and g) a button for viewing data about the action. In the example, data 712, which is a patient record, is associated with the update only action in the second audit record of the three audit records which are returned.

In the examples, audit records from three different employees are returned at different times. The employees each utilized different modules associated with the MPI system. Three actions, a search, update only and registration were captured as part of the audit records. In the earliest action, a patient was registered. In the next action, the record was updated. Finally, in the latest action, a search returned a result including the record in the first two actions.

Figure 12:
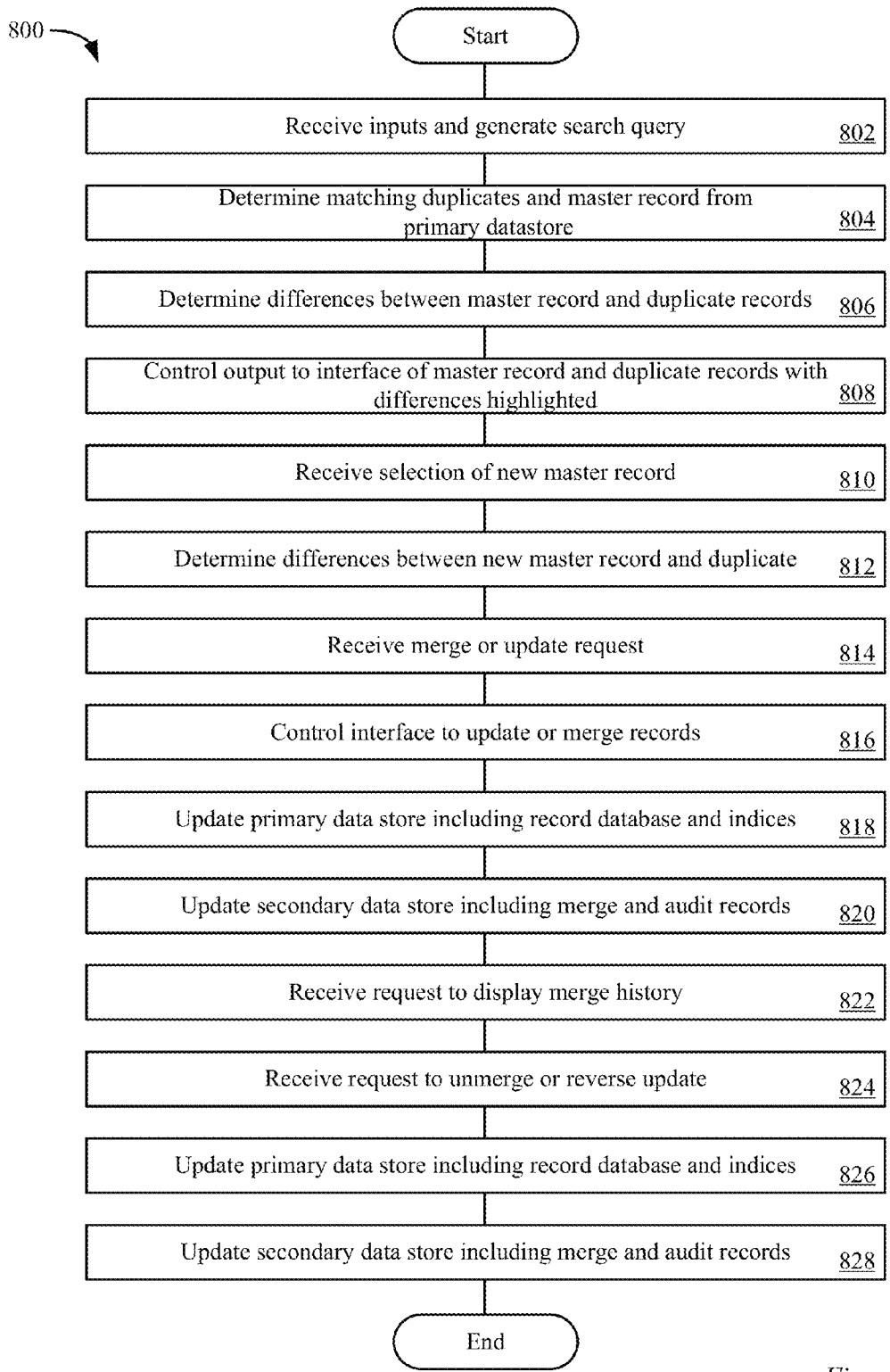
FIG. 12 is a flow chart of a method of modifying duplicate records in accordance with the described embodiments.

Next, a method of modifying duplicate records in an MPI system is described. FIG. 12 is a flow chart of a method 800 of modifying duplicate records. In 802, search input terms can be received and a search query can be constructed for searching the inverted indices of an MPI system database using the received inputs. In 804, the entire MPI database can be searched. Records matching all or a portion of the query can be identified and a duplicate matching score can be generated for each records returned in response to the query. In one embodiment, the returned records can be sorted according to their duplicate matching score. In particular, a record with the highest score may be designated as the master record.

In 806, when multiple records are returned, differences in field values between the master record and the duplicate records can be determined on a field by field basis. In one embodiment, the interface is configured to receive a designation of another record as a master record. After such a designation, differences between the newly selected master record and the duplicate records can be determined.

In 808, the system can be configured to control output of an interface on an output device, such as a display device. In one embodiment, the display device can be associated with a client side device in communication with a remote server which controls output to the interface and accesses the MPI system data stores. In one embodiment, via the interface, information associated with fields in the master record and the duplicate records can be simultaneously output on the output device. Further, differences between the master record and the duplicate records can be graphically highlighted in some manner.

In 810, a new master record can be selected from the records returned with the current search or a new search can be carried out which results in a different master record. When a new search is carried out, the information which linked a group of records is not retained and is deleted. In 812, the differences between the new master record and one or more duplicate records can be determined. Then, field information associated with the master record and the one or more duplicate records can be output simultaneously where differences in information between the master record and duplicate records.

In 814, a request to modify a record, such as a merge or update request, can be received. In 816, the interface can be controlled to allow a user to merge and update records. For example, the user may be able to drag and drop information from one record to another record. In another example, a free text box can be provided for entering information in a particular field. In one embodiment, the system can be configured to perform an auto-merge if two records meet some criterion for designation as duplicate records. In this example, the system may save the merge information so that a person can later review and approve of the automatic merge.

In 818, after a record is updated, the primary data store can be updated. For example, if the merge resulted in one of the records being deleted, then the deleted record can be removed from the data store. In response to a change in the field values associated with a record, inverted indices associated with an MPI database can be updated. For example, when a person with a last name which has never appeared in the database is registered then the new name and a pointer to the record containing the new name can be added to the inverted index for the last name field. In another example, if name is already in the inverted index, then a pointer to the new record can associated with the name string already existing in the inverted index.

In 820, in one embodiment, a secondary data store including merge and audit records can be updated when the record in the primary data store is updated. The merge and audit records may allow changes to a record to be reversed and the type of changes made to be recalled. When the merge and audit information is stored in a data store separate from the MPI database records, searches of the MPI database records are accelerated.

In 822, via the interface, a request to display a merge history for a record can be received and the merge history associated with the record can be displayed. In 824, a request to unmerge two records or reverse an update to a record can be received. In response, the unmerged records or state of a record prior to an update can be output to the interface. When the action is approved, such as an unmerge, in 826, the primary data store including the MPI database and the inverted indices associated with the MPI database can be update. In 828, a secondary data store including the merge and audit records which reflect the changes implemented in 824 can be updated.

Embodiments of the present invention further relate to computer readable media that include executable program instructions. The media and program instructions may be those specially designed and constructed for the purposes of the present invention, or any kind well known and available to those having skill in the computer software arts. When executed by a processor, these program instructions are suitable to implement any of the methods and techniques, and components thereof, described above. Examples of computer-readable media include, but are not limited to, magnetic media such as hard disks, semiconductor memory, optical media such as CD-ROM disks; magneto-optical media such as optical disks; and hardware devices that are specially configured to store program instructions, such as read-only memory devices (ROM), flash memory devices, EEPROMs, EPROMs, etc. and random access memory (RAM). Examples of program instructions include both machine code, such as produced by a compiler, and files containing higher-level code that may be executed by the computer using an interpreter. The media including the executable program instructions can be executed on servers or other computation devices including processors and memory.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed. It will be apparent to one of ordinary skill in the art that many modifications and variations are possible in view of the above teachings.

While the embodiments have been described in terms of several particular embodiments, there are alterations, permutations, and equivalents, which fall within the scope of these general concepts. It should also be noted that there are many alternative ways of implementing the methods and apparatuses of the present embodiments. It is therefore intended that the following appended claims be interpreted as including all such alterations, permutations, and equivalents as fall within the true spirit and scope of the described embodiments.

What is claimed is:

1. A method of managing electronic protected healthcare information comprising:
receiving, by a processor, a plurality of healthcare records having electronic protected healthcare information wherein each healthcare record is configured with a plurality of different fields each field configured to receive at least one value, the plurality of different fields including a first name field, a last name field, a date of birth filed, a sex field, a housing address field and at least one field associated with a personal identification instrument wherein the healthcare record is configured to store information related to a plurality of different personal identification instruments and wherein the plurality of health care records is at least ten thousand;

generating a master patient index database in an inverted index format, wherein, in the inverted index format, a set of values is determined which is inclusive of all values appearing in the first name field, the last name field, the date of birth field, the sex field, the housing address field and the at least one field of the at least ten thousand healthcare records such that each value in the set of values is mapped to one or more of the plurality of healthcare records;

determining and storing, by the processor, physical locations of each of the plurality of the healthcare records in a memory device;

outputting to a display an interface which includes areas where search terms values that are input are displayed;

receiving, via an input mechanism communicatively coupled to the processor, one or more search input terms;

based upon the one or more search inputs terms, generating, in the processor, a search query and searching, using the search query, the set of values inclusive of all values appearing in the first name field, the last name field, the date of birth field, the sex field, the housing address field and the at least one field of the at least ten thousand healthcare records in the inverted index format of the master patient index database to identify a subset of values in the set of values which match the search query;

determining, by the processor, using the inverted index format of the master patient index database, a set of healthcare records associated with each of the subset of values;

determining, by the processor, for each of the subset of the values, a contribution to a duplicate probability score wherein information is stored with each personal identification instrument which indicates that the personal instrument is active or inactive and wherein the contribution to the duplicate probability score depends upon whether each personal identification instrument which is matched to the search query is indicated as active or inactive;

based upon the determined contributions to the duplicate probability score and the set of the healthcare records determined to be associated with each of the subset of the values, determining, by the processor, for two or more healthcare records in the set of healthcare records identified via the search query a total duplicate probability score;

retrieving, using the physical locations for the two or more healthcare records, values associated with the two or more healthcare records; and outputting, by the processor, to the display the total duplicate probability score and electronic protected healthcare information for each of the two or more healthcare records including the values associated with the first name, the last name, the date of birth, the sex, the housing address and the at least one field.

2. The method of claim 1, further comprising, based upon the total duplicate probability scores, determining, by the processor, the two or more healthcare records are duplicate health records.

3. The method of claim 1, further comprising receiving scoring thresholds associated with the total duplicate probability score and based upon the scoring thresholds, categorizing two or more healthcare records.

4. The method of claim 1, wherein at least one category is an indication of a match.

5. The method of claim 1, wherein the set of values is inclusive of all values appearing in a plurality of different fields of the healthcare records.

6. The method of claim 1, further comprising:
receiving a new healthcare record;
determining a first value in the at least one field of the new healthcare record matches a second value in the set of values; and
updating the second value in inverted index format of the master patient index database so that the second value points to the new healthcare record.

7. The method of claim 6, wherein the new healthcare record is received as a part of a registration of a new patient.

8. The method of claim 1, further comprising:
receiving a new healthcare record,
determining a first value in the at least one field of the new healthcare is not one of the set of values; and
updating the set of values in the inverted index form of the master patient index database so that the first value is added to the set of values and the first value points to the new healthcare record.

9. The method of claim 1, further comprising:
deleting one of the plurality of healthcare records;
determining a first value in the at least one field of the deleted healthcare record matches a second value in the set of values; and
updating the second value so that it no longer points to the deleted healthcare record.

10. The method of claim 9, further comprising:
determining the second value only points to the deleted healthcare record and deleting the second value from the set of values.

11. The method of claim 1, wherein the at least one field is selected from the group consisting of a last name, a first name, a nickname, a facility identifier, a personal identification instrument, a sex, a date of birth, a social security number, a first address, a second address, a city, a state, a postal code, a phone number, an e-mail address and a race.

12. The method of claim 1, wherein a type of the personal identification instrument is stored with each of the personal identification instruments, said type selected from a plurality of different types, and wherein the contribution to the duplicate probability score depends on the type of the personal identification instrument which is matched to the search query.

13. The method of claim 1, wherein the at least one field is associated with an e-mail address and the healthcare record is configured to store a plurality of different e-mail addresses.

14. The method of claim 13, wherein information is stored with each e-mail address which indicates that the e-mail address is active or inactive and wherein the contribution to the duplicate probability score depends upon whether each e-mail address matched to the search query is active or inactive.

15. The method of claim 1, wherein the at least one field is associated with phone number and the healthcare record is configured to store a plurality of different phone numbers.

16. The method of claim 15, wherein information is stored with each phone number which indicates that the phone is active or inactive and wherein the contribution to the duplicate probability score depends upon whether each phone number matched to the search query is active or inactive.

17. The method of claim 1, wherein the at least one field is associated with a housing address and the healthcare record is configured to store a plurality of different housing addresses.

18. The method of claim 17, wherein information is stored with each housing address which indicates that the housing address is active or inactive and wherein the contribution to the duplicate probability score depends upon whether each housing address matched to the search query is active or inactive.

19. The method of claim 1, further comprising
receiving a plurality of different search queries each associated with a different user;
determining a custom set of scoring parameters for each user used to determine the contributions to the duplicate probability; and
determining the total duplicate probability score for each search query using the custom set of scoring parameters determined for each user
wherein the inverted index format of the master patient index database is used for each of the search queries.

20. The method of claim 1, wherein the plurality of healthcare records includes a first portion of the healthcare records and a second portion of the healthcare records wherein a first set of scoring parameters is used to determine the contributions to the duplicate probability score for the first portion of the healthcare records and a second set of scoring parameters is used to determine the contributions to the duplicate probability score for the second portion of the healthcare records.

21. A method of managing electronic protected healthcare information comprising:
receiving, by a processor, a plurality of healthcare records having electronic protected healthcare information wherein each healthcare record is configured with a plurality of different fields each field configured to receive at least one value, the plurality of different fields including a first name field, a last name field, a date of birth field, a sex field, a housing address field and
at least one field associated with an e-mail address wherein the each healthcare record is configured to store a plurality of different e-mail addresses and wherein the plurality of health care records is at least ten thousand;
generating a master patient index database in an inverted index format, wherein, in the inverted index format, a set of values is determined which is inclusive of all values appearing in the first name field, the last name field, the date of birth field, the sex filed, the housing address field and the at least one field of the at least ten thousand healthcare records such that each value in the set of values is mapped to one or more of the plurality of healthcare records;
determining and storing, by the processor, physical locations of each of the plurality of the healthcare records in a memory device;
outputting to a display an interface which includes areas where search terms values that are input are displayed;
receiving, via an input mechanism communicatively coupled to the processor, one or more search input terms;
based upon the one or more search inputs terms, generating, in the processor, a search query and searching, using the search query, the set of values inclusive of all values appearing in the first name field, the last name field, the date of birth field, the sex field, the housing address field and the at least one field of the at least ten thousand healthcare records in the inverted index format of the master patient index database to identify a subset of values in the set of values which match the search query;
determining, by the processor, using the inverted index format of the master patient index database, a set of healthcare records associated with each of the subset of values;
determining, by the processor, for each of the subset of the values, a contribution to a duplicate probability score
wherein information is stored with each e-mail address which indicates that the e-mail address is active or inactive and wherein the contribution to the duplicate probability score depends upon whether each e-mail address matched to the search query is active or inactive;
based upon the determined contributions to the duplicate probability score and the set of the healthcare records determined to be associated with each of the subset of the values, determining, by the processor, for two or more healthcare records in the set of healthcare records identified via the search query a total duplicate probability score;
retrieving, using the physical locations for the two or more healthcare records, values associated with the two or more healthcare records; and
outputting, by the processor, to the interface on the display, the total duplicate probability score and electronic protected healthcare information for each of the two or more healthcare records including the values associated with the first name, the last name, the date of birth, the sex, the housing address and the at least one field.

22. A method of managing electronic protected healthcare information comprising:
receiving, by a processor, a plurality of healthcare records having electronic protected healthcare information wherein each healthcare record is configured with a plurality of different fields each field configured to receive at least one value, the plurality of different fields including a first name field, a last name field, a date of birth field, a sex field, a housing address field and
at least one field associated with phone number wherein the healthcare record is configured to store a plurality of different phone numbers and wherein the plurality of health care records is at least ten thousand;
generating a master patient index database in an inverted index format, wherein, in the inverted index format, a set of values is determined which is inclusive of all values appearing in at least one field of the at least ten thousand healthcare records such that each value in the set of values is mapped to one or more of the plurality of healthcare record;
determining and storing, by the processor, physical locations of each of the plurality of the healthcare records in a memory device;
outputting to a display an interface which includes areas where search terms values that are input are displayed;
receiving, via an input mechanism communicatively coupled to the processor, one or more search input terms;
based upon the one or more search inputs terms, generating, in the processor, a search query and searching, using the search query, the set of values inclusive of all values appearing in the first name field, the last name field, the date of birth field, the sex field, the housing address field and the at least one field of the at least ten thousand healthcare records in the inverted index format of the master patient index database to identify a subset of values in the set of values which match the search query;
determining, by the processor, using the inverted index format of the master patient index database, a set of healthcare records associated with each of the subset of values;

determining, by the processor, for each of the subset of the values, a contribution to a duplicate probability score wherein information is stored with each phone number which indicates that the phone is active or inactive and wherein the contribution to the duplicate probability score depends upon whether each phone number matched to the search query is active or inactive;

based upon the determined contributions to the duplicate probability score and the set of the healthcare records determined to be associated with each of the subset of the values, determining, by the processor, to the interface on the display, for two or more healthcare records in the set of healthcare records identified via the search query a total duplicate probability score;

retrieving, using the physical locations for the two or more healthcare records, values associated with the two or more healthcare records; and outputting, by the processor, to the display, the total duplicate probability score and electronic protected healthcare information for each of the two or more healthcare records including the values associated with the first name field, the last name field, the date of birth field, the sex field, the housing address field and the at least one field.

23. A method of managing electronic protected healthcare information comprising:

receiving, by a processor, a plurality of healthcare records having electronic protected healthcare information wherein each healthcare record is configured with a plurality of different fields each field configured to receive at least one value, the plurality of different fields including a first name field, a last name field, a date of birth filed, a sex field and the at least one field is associated with a housing address and the healthcare record is configured to store a plurality of different housing addresses and wherein the plurality of health care records is at least ten thousand;

generating a master patient index database in an inverted index format, wherein, in the inverted index format, a set of values is determined which is inclusive of all values appearing in at least one field of the at least ten thousand healthcare records such that each value in the set of values is mapped to one or more of the plurality of healthcare records;

determining and storing, by the processor, physical locations of each of the plurality of the healthcare records in a memory device;

outputting to a display an interface which includes areas where search terms values that are input are displayed;

receiving, via an input mechanism communicatively coupled to the processor, one or more search input terms;

based upon the one or more search inputs terms, generating, in the processor, a search query and searching, using the search query, the set of values inclusive of all values appearing in the first name field, the last name field, the date of birth field, the sex field and the at least one field of the at least ten thousand healthcare records to identify a subset of values in the set of values which match the search query;

determining, by the processor, using the inverted index format of the master patient index database, a set of healthcare records associated with each of the subset of values;

determining, by the processor, for each of the subset of the values, a contribution to a duplicate probability score wherein information is stored with each housing address which indicates that the housing address is active or inactive and wherein the contribution to the duplicate probability score depends upon whether each housing address matched to the search query is active or inactive;

based upon the determined contributions to the duplicate probability score and the set of the healthcare records determined to be associated with each of the subset of the values, determining, by the processor, for two or more healthcare records in the set of healthcare records identified via the search query a total duplicate probability score;

retrieving, using the physical locations for the two or more healthcare records, values associated with the two or more healthcare records;

outputting, by the processor, to the display, the total duplicate probability score and electronic protected healthcare information for each of the two or more healthcare records including the values associated with the first name field, the last name field, the date of birth field, the sex field and the at least one field.

24. A method of managing electronic protected healthcare information comprising:

receiving, by a processor, a plurality of healthcare records having electronic protected healthcare information wherein each healthcare record is configured with a plurality of different fields each field configured to receive at least one value, the plurality of different fields including a first name field, a last name field, a date of birth filed, a sex field and a housing address field wherein the plurality of health care records is at least ten thousand;

generating a master patient index database in an inverted index format, wherein, in the inverted index format, a set of values is determined which is inclusive of all values appearing in at least one field of the ten thousand healthcare records such that each value in the set of values is mapped to one or more of the plurality of healthcare records;

determining and storing, by the processor, physical locations of each of the plurality of the healthcare records in a memory device;

outputting to a display an interface which includes areas where search terms values that are input are displayed;

receiving, via an input mechanism communicatively coupled to the processor, one or more search input terms;

based upon the one or more search inputs terms, generating, in the processor, a search query and searching, using the search query, the set of values inclusive of all values appearing in the first name field, the last name field, the date of birth field, the sex field and the housing address field of the at least ten thousand healthcare records in the inverted index format of the master patient index database to identify a subset of values in the set of values which match the search query;

determining, by the processor, using the inverted index format of the master patient index database, a set of healthcare records associated with each of the subset of values;

determining, by the processor, for each of the subset of the values, a contribution to a duplicate probability score;

based upon the determined contributions to the duplicate probability score and the set of the healthcare records determined to be associated with each of the subset of the values, determining, by the processor, for two or more healthcare records in the set of healthcare records identified via the search query a total duplicate probability score;

retrieving, using the physical locations for the two or more healthcare records, values associated with the two or more healthcare records;

outputting, by the processor, to the display the total duplicate probability score and electronic protected healthcare information for each of the two or more healthcare records including the values associated with the first name field, the last name field, the date of birth field, the sex field and the housing address field;

receiving a plurality of different search queries each associated with a different user;

determining a custom set of scoring parameters for each user used to determine the contributions to the duplicate probability; and determining the total duplicate probability score for each search query using the custom set of scoring parameters determined for each user wherein the inverted index format of the master patient index database is used for each of the search queries.

* * * * *